United States Patent
Tsang et al.

(10) Patent No.: US 9,839,694 B2
(45) Date of Patent: Dec. 12, 2017

(54) REDUCTION OF ENDOTOXINS FROM POLYANIONIC POLYMER CONJUGATES

(71) Applicant: NITTO DENKO CORPORATION, Osaka (JP)

(72) Inventors: Kwok Yin Tsang, Irvine, CA (US); Hao Bai, San Diego, CA (US); Yi Jin, Carlsbad, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 14/786,729

(22) PCT Filed: Apr. 26, 2013

(86) PCT No.: PCT/US2013/038501
§ 371 (c)(1),
(2) Date: Oct. 23, 2015

(87) PCT Pub. No.: WO2014/175899
PCT Pub. Date: Oct. 30, 2014

(65) Prior Publication Data
US 2016/0058877 A1    Mar. 3, 2016

(51) Int. Cl.
| | |
|---|---|
| C08G 69/00 | (2006.01) |
| A61K 47/48 | (2006.01) |
| A61K 31/337 | (2006.01) |
| C08G 69/10 | (2006.01) |
| C08G 69/46 | (2006.01) |
| C08G 69/48 | (2006.01) |
| A61K 47/59 | (2017.01) |
| A61K 47/64 | (2017.01) |

(52) U.S. Cl.
CPC ...... *A61K 47/48207* (2013.01); *A61K 31/337* (2013.01); *A61K 47/595* (2017.08); *A61K 47/645* (2017.08); *C08G 69/10* (2013.01); *C08G 69/46* (2013.01); *C08G 69/48* (2013.01)

(58) Field of Classification Search
None
See application file for complete search history.

(56) References Cited

U.S. PATENT DOCUMENTS

| | | | |
|---|---|---|---|
| 2002/0077279 A1 | 6/2002 | Kumar et al. | |
| 2007/0128118 A1* | 6/2007 | Yu | A61K 47/48238 424/9.322 |
| 2012/0052015 A1 | 3/2012 | Yu et al. | |

FOREIGN PATENT DOCUMENTS

| | | |
|---|---|---|
| JP | 2009-518511 | 5/2009 |
| WO | WO 2007/067417 | 6/2007 |
| WO | WO 2008/124735 | 10/2008 |

OTHER PUBLICATIONS

International Search Report dated Jul. 29, 2013 in International Application No. PCT/US2013/038501, filed on Apr. 26, 2013.
IUPAC-IUP Commission of Biochemical Nomenclature Biochem. vol. 11: 942-944 1972.
Extended European Search Report Communication for EPO Application 13882935.3 PCT/US2013038501 dated Dec. 15, 2016.
Office Action dated Mar. 31, 2017 issued in Japanese Patent Application No. 2016-510658, filed Feb. 24, 2014.
Office Action dated Jun. 23, 2017 Issued in Japanese Patent Application No. 2016-510658, filed Feb. 24, 2014.

* cited by examiner

*Primary Examiner* — Ana L Woodward
(74) *Attorney, Agent, or Firm* — Knobbe, Martens, Olson & Bear, LLP

(57) ABSTRACT

Described herein are methods of lowering the endotoxin content from a polyanionic polymer conjugate. In particular, methods of reducing the endotoxin content from a polyanionic polymer conjugate that can be useful for a variety of drug delivery applications are described herein.

42 Claims, 4 Drawing Sheets

REDUCTION OF ENDOTOXINS FROM POLYANIONIC POLYMER CONJUGATES

BACKGROUND

Field

This application relates generally to methods of reducing the endotoxin content from a polyanionic polymer conjugate. In particular, the application relates to lowering the endotoxin content from a polyanionic polymer conjugate that can be useful for a variety of drug delivery applications.

Description

Amino acid-based polymers have been considered as a potential source of new biomaterials. Poly-amino acids having good biocompatibility have been investigated to deliver low molecular-weight compounds. A relatively small number of polyglutamic acids and copolymers have been identified as candidate materials for drug delivery.

SUMMARY

Some embodiments described herein generally relate to a method of purifying a polyanionic polymer conjugate that can include combining a starting polyanionic polymer conjugate with a first solvent system to form a solution; precipitating a portion of the starting polyanionic polymer conjugate by lowering a pH of the solution; and washing the precipitated polyanionic polymer conjugate with a second solvent system, wherein one or both of the first solvent system and the second solvent system comprises a water miscible organic solvent, to provide a purified polyanionic polymer conjugate, wherein the amount of endotoxin present in the purified polyanionic polymer conjugate is less than the amount of endotoxin present in the starting polyanionic polymer conjugate.

Some embodiments described herein are generally relate to a method of purifying a poly(γ-L-glutamyl-glutamate)-polymer conjugate, poly(glutamate)-polymer conjugate, poly(γ-L-glutamyl-asparate)-polymer conjugate, poly(asparate)-polymer conjugate, poly(L-aspartyl-glutamate)-polymer conjugate, poly(L-aspartyl-asparate)-polymer conjugate and copolymers thereof, that can include combining a one of the aforementioned starting polymer conjugates with a first solvent system to form a solution; precipitating a portion of the starting polymer conjugate by lowering a pH of the solution; and washing the precipitated polymer conjugate with a second solvent system, wherein one or both of the first solvent system and the second solvent system comprises a water miscible organic solvent, to provide a one of the aforementioned purified polymer conjugate, wherein the amount of endotoxin present in the purified polymer conjugate is less than the amount of endotoxin present in the starting polymer conjugate.

Some embodiments described herein are generally relate to a method of purifying a poly(γ-L-glutamyl-glutamate)-polymer conjugate that can include combining a starting poly(γ-L-glutamyl-glutamate)-polymer conjugate with a first solvent system to form a solution; precipitating a portion of the starting poly(γ-L-glutamyl-glutamate)-polymer conjugate by lowering a pH of the solution; and washing the precipitated poly(γ-L-glutamyl-glutamate)-polymer conjugate with a second solvent system, wherein one or both of the first solvent system and the second solvent system comprises a water miscible organic solvent, to provide a purified poly(γ-L-glutamyl-glutamate)-polymer conjugate, wherein the amount of endotoxin present in the purified poly(γ-L-glutamyl-glutamate)-polymer conjugate is less than the amount of endotoxin present in the starting poly(γ-L-glutamyl-glutamate)-polymer conjugate.

DETAILED DESCRIPTION

Definitions

Figure 1:
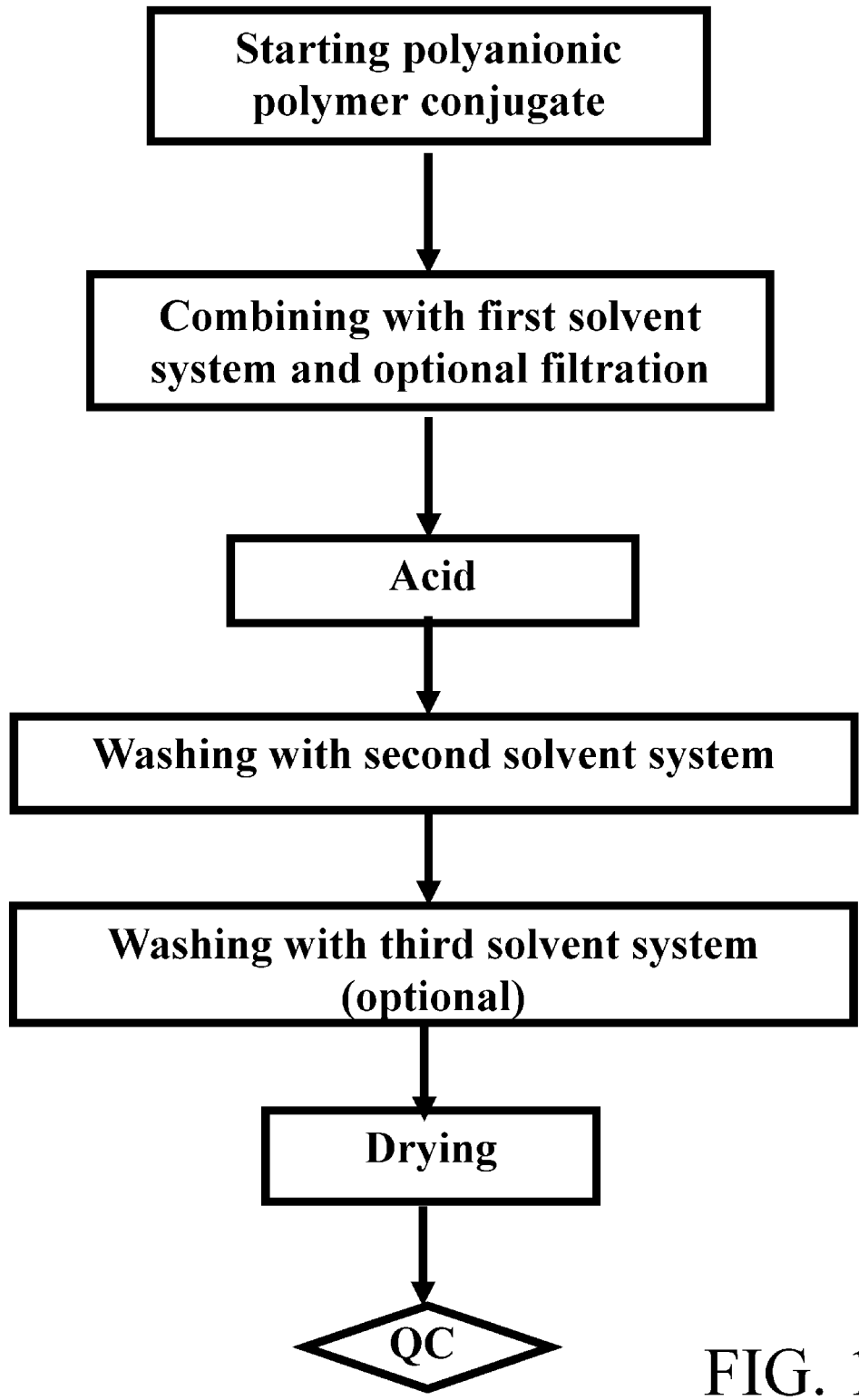
FIG. 1 outlines an example procedure for reducing the endotoxin content of a polyanionic polymer conjugate.
Figure 2:
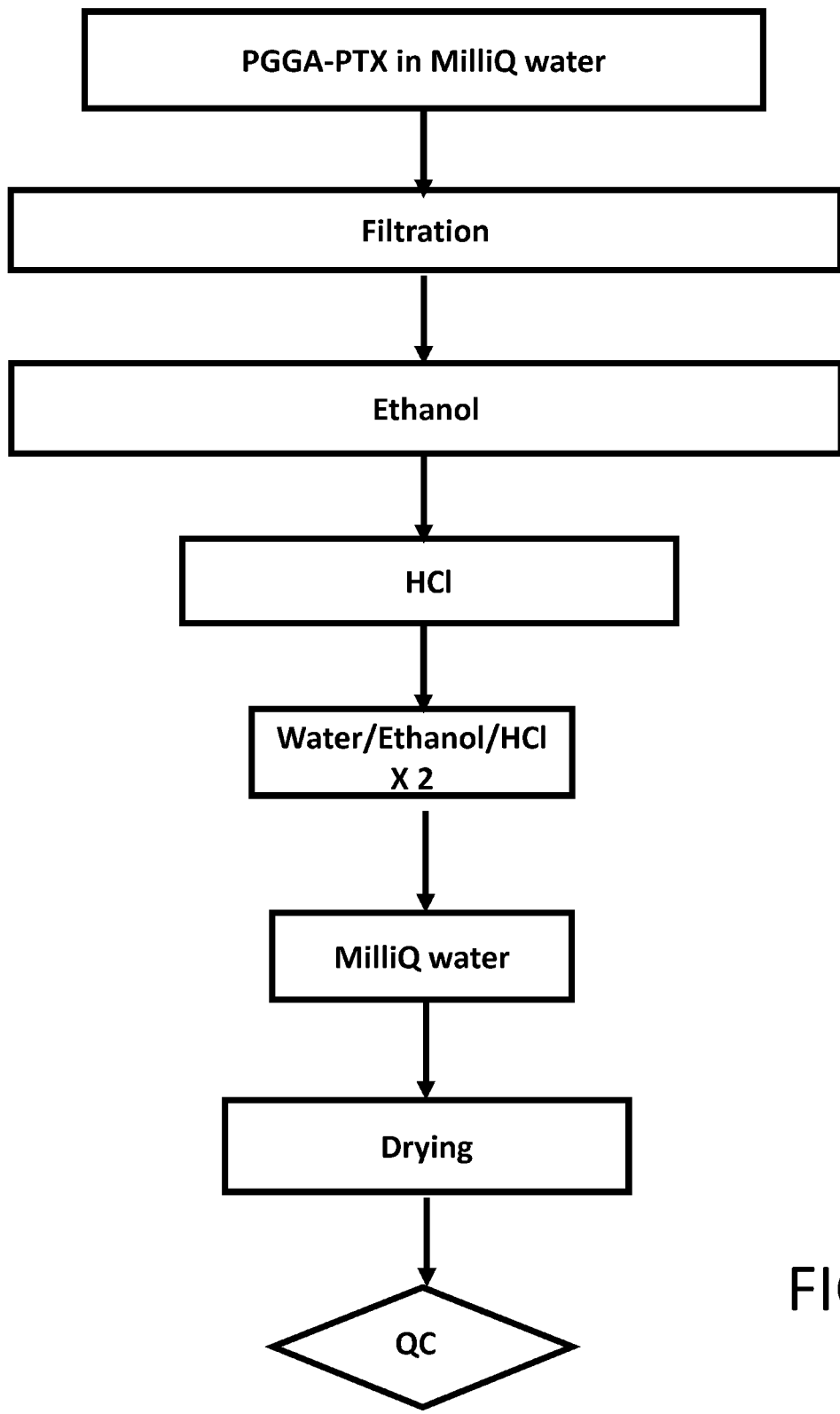
FIG. 2 outlines an example procedure for reducing the endotoxin content of PGGA-PTX.
Figure 3:
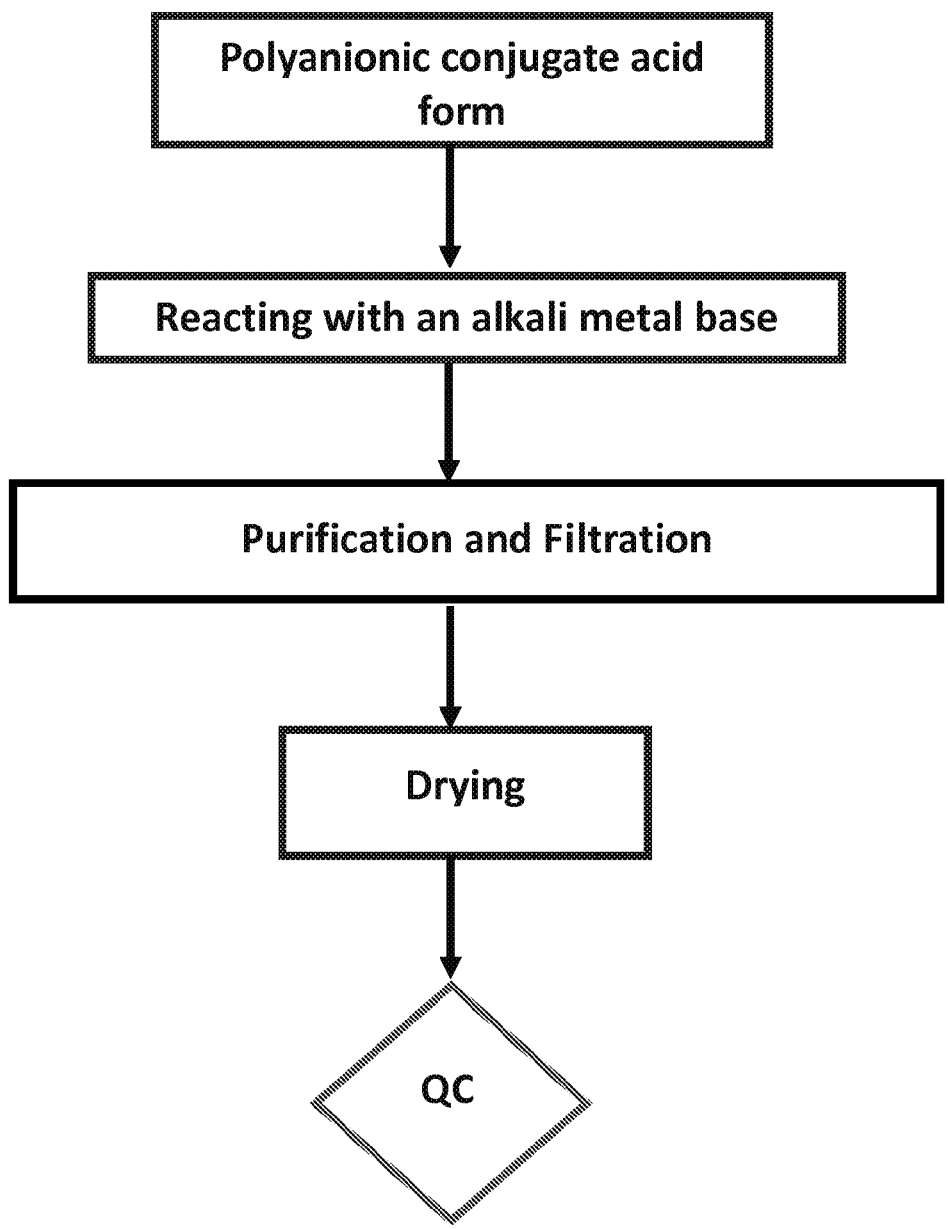
FIG. 3 outlines an example procedure for converting a polyanionic polymer conjugate from its acid form to its salt form.
Figure 4:
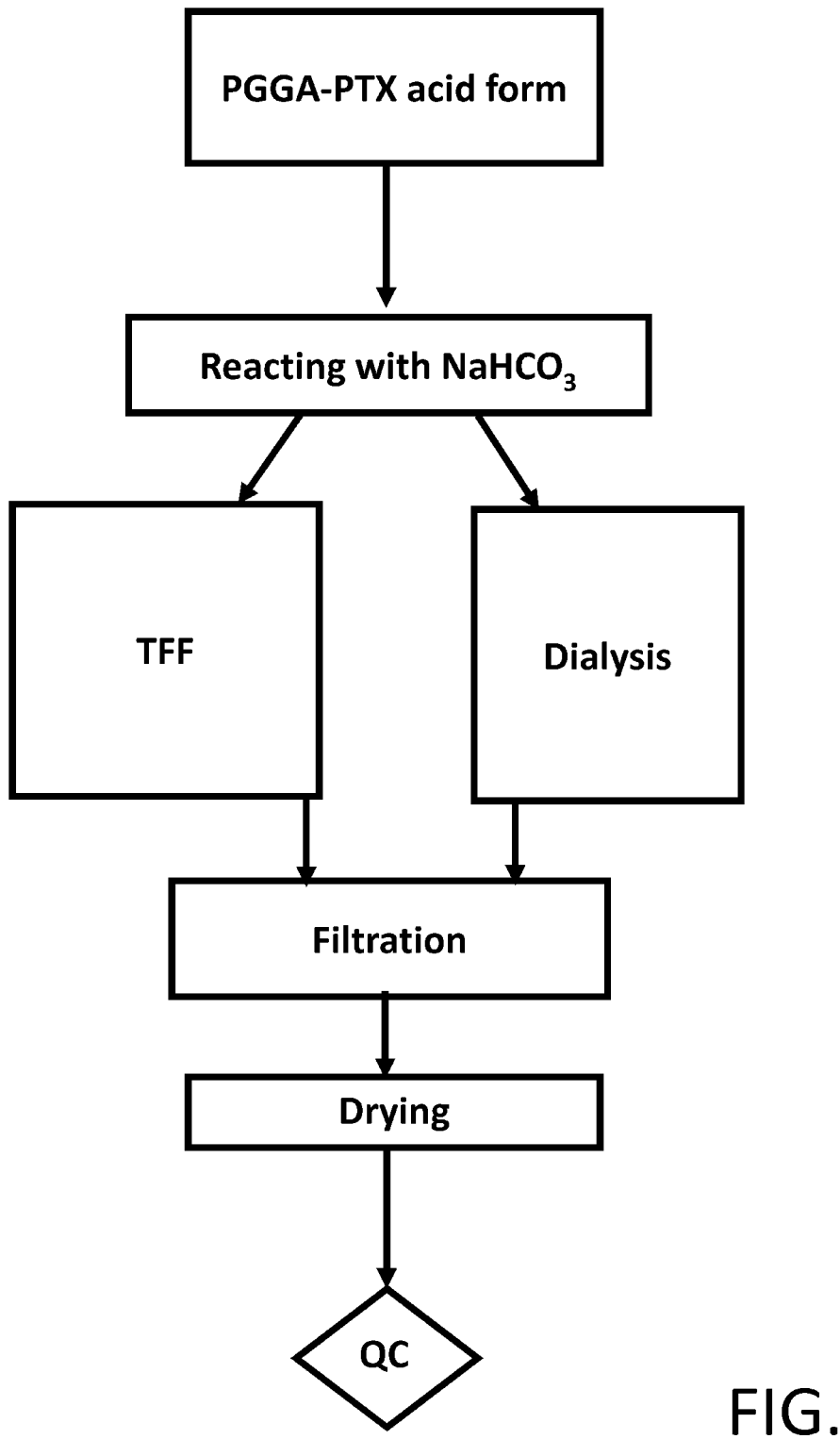
FIG. 4 outlines an example procedure for converting PGGA-PTX from its acid form to its salt form.

Unless defined otherwise, all technical and scientific terms used herein have the same meaning as is commonly understood by one of ordinary skill in the art. All patents, applications, published applications and other publications referenced herein are incorporated by reference in their entirety, unless stated otherwise. In the event that there is a plurality of definitions for a term, those in this section prevail unless stated otherwise.

As used herein, the term "water-soluble" describes a compound that can be completely dissolved in water at a concentration at least of 3 grams per 100 mL of water at pH equal to 7. See Shriner at al., The Systematic Identification of Organic Compounds, §5.1.1, ($6^{th}$ ed. 1980).

The term "polymer" is used herein includes both homopolymers and copolymers having various molecular architectures, unless stated otherwise.

The term "polymer-conjugate" describes polymers that are attached to one or more types of biologically active agents or drugs, such as paclitaxel. For example, PGGA-PTX as used herein is a polymer conjugate in which poly-(γ-L-glutamyl-glutamate) (PGGA) is attached to paclitaxel (PTX). Examples for suitable biologically useful agents include, but are not limited to, a targeting agent, an imaging agent (for example, an optical imaging or a magnetic resonance imaging agent) and a stabilizing agent (such as polyethylene glycol). The biologically useful agent and/or drug may be attached directly to the suitable molecule (such as, PTX), or the suitable molecule may be attached directly to the polymer of via a linker group. The linker group may be a relatively small chemical moiety such as an ester, amide or amine bond, or may be a larger chemical moiety, e.g., an alkyl ester linkage or an alkylene oxide linkage.

Examples of targeting agents include an arginine-glycine-aspartate (RGD) peptide, cyclic (fKRGD), fibronectin, folate, galactose, an apolipoprotein, insulin, transferrin, a fibroblast growth factor (FGF), an epidermal growth factor (EGF) and an antibody. A targeting agent can interact with a receptor selected from $α_v,β_3$-integrin, folate, asialoglycoprotein, a low-density lipoprotein (LDL), an insulin receptor, a transferrin receptor, a fibroblast growth factor (FGF) receptor, an epidermal growth factor (EGF) receptor and an antibody receptor.

Examples of optical imaging agents include an acridine dye, a coumarine dye, a rhodamine dye, a xanthene dye, a cyanine dye, and a pyrene dye. Specific optical imaging agents include Texas Red, Alexa Fluor® dye, BODIPY® dye, Fluorescein, Oregon Green® dye, and Rhodamine Green™ dye.

Examples of magnetic resonance imaging agents can include a paramagnetic metal compound (for example Gd(III)), such as

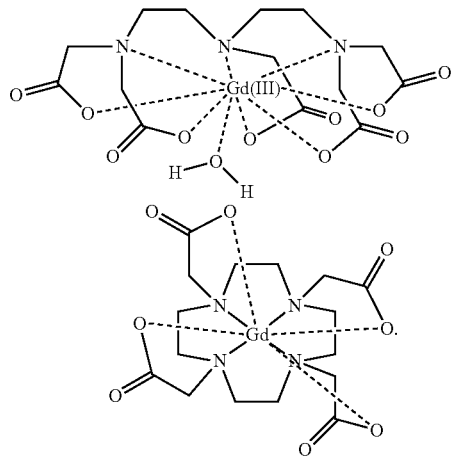

and

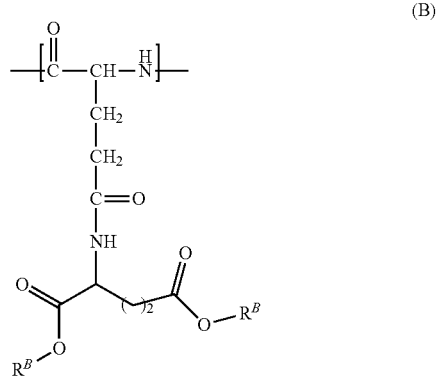

The term "polyanionic polymer conjugate" as used herein describes a polymer conjugate that is negatively charged at neutral pH (i.e. pH=7). Examples of polyanionic polymer conjugates include, but are not limited to, poly-(γ-L-glutamyl-glutamate) polymer conjugates, poly(glutamate) polymer conjugates, poly(aspartate) polymer conjugates, poly(γ-L-glutamyl-aspartate) polymer conjugates, poly(aspartyl-aspartate) polymer conjugates, poly(aspartyl-glutamate) polymer conjugates, poly(asparate) polymer conjugates and copolymers thereof.

As used herein poly(glutamyl-aspartate) (PGAA) refers to a polymer that consists of, or consists essentially of, recurring units of Formula (A), wherein: each $R^A$ can be independently hydrogen or an alkali metal. The recurring units of the Formula (A) can be in the form of a salt, e.g., a sodium salt, or an acid. Thus, as used herein, poly(glutamyl-aspartate) refers to a polymer that can contain the acid form of Formula (A), the salt form of Formula (A), or both, unless stated otherwise.

(A)

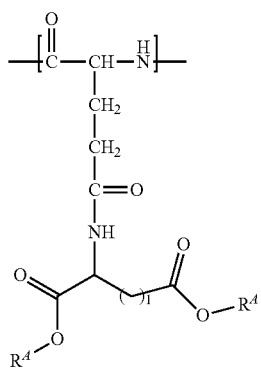

As used herein poly-(γ-L-glutamyl-glutamate) (PGGA) refers to a polymer that consists of, or consists essentially of, recurring units of Formula (B) as described herein, wherein: each $R^B$ can be independently hydrogen or an alkali metal. The recurring units of Formula (B) can be in the form of a salt, e.g., a sodium salt, or an acid. Thus, as used herein, poly(glutamyl-glutamate) refers to a polymer that can contain the acid form of Formula (B), the salt form of Formula (B), or both, unless stated otherwise.

As used herein poly(aspartate) (PA) refers to a polymer that consists of, or consists essentially of, recurring units of Formula (C), Formula (D), or both, wherein each $R^C$ and each $R^D$ can be independently hydrogen or an alkali metal. Some of the poly(aspartate) may be in the form of a salt, e.g., a sodium salt, or an acid. The recurring units of Formula (C) and/or Formula (D) can be in the form of a salt, e.g., a sodium salt, or an acid. Thus, as used herein, poly(aspartate) refers to a polymer that can contain the acid form of Formula (C) and/or Formula (D), the salt form of Formula (C) and/or Formula (D), or both, unless stated otherwise.

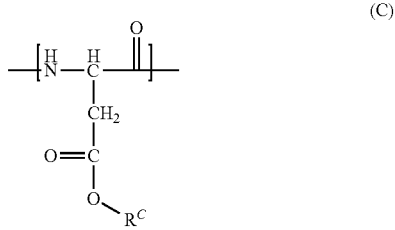

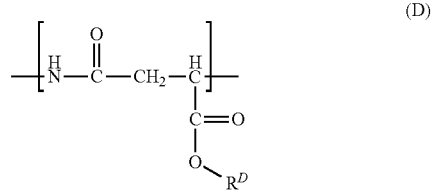

As used herein poly(glutamate) (PGA) refers to a polymer that consists of, or consists essentially of, recurring units of Formula (E), Formula (F) or both, wherein each $R^E$ and each $R^F$ can be independently hydrogen or an alkali metal. The recurring units of Formula (E) and/or Formula (F) can be in the form of a salt, e.g., a sodium salt, or an acid. Thus, as used herein, poly(glutamate) refers to a polymer that can contain the acid form of Formula (E) and/or Formula (F), the salt form of Formula (E) and/or Formula (F), or both, unless stated otherwise.

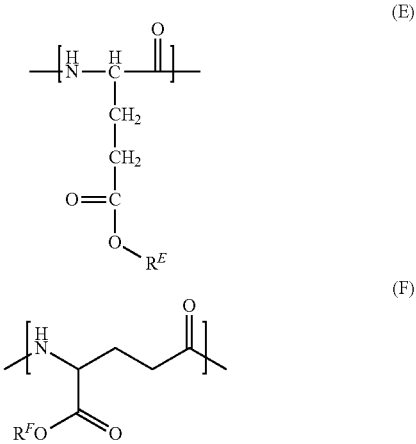

As used herein, "$C_m$ to $C_n$," in which "m" and "n" are integers that refer to the number of carbon atoms in a group or the number of carbons in a ring(s). That is, the group or ring can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH_3)CH_2$— and $(CH_3)_3C$—. If no "m" and "n" are designated, the broadest range described in the definitions provided herein is to be assumed.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

Methods of Lowering Endotoxin Levels

Some embodiments described herein generally relate to a method of lowering the endotoxin content present in a polyanionic polymer conjugate. Endotoxins, also called lipopolysaccharides (LPS), are major contaminants found in commercially available proteins or biologically active substances. The presence of endotoxins often complicates study of the biological effects of the main ingredient. The presence of a small amount of endotoxins in recombinant protein preparations can cause side effects in host organism such as endotoxin shock, tissue injury, and even death. Therefore, it is important to remove endotoxins from drugs, injectables, and other biological and pharmaceutical products.

A major source of the endotoxins in polyanionic polymer conjugates can be attributed to the large quantity of water utilized in tangential flow filtration (TFF) purification. High quality endotoxin-free water-for-injection (WFI) can be used in TFF purification; however, the operational cost for large scale purification can be very high, such that large scale purification is cost prohibitive.

Other procedures for generating products with low-endotoxin levels are known. However, none of the procedures are broadly applicable. For example, anionic-exchange chromatography is potentially useful for decontamination of positively-charged proteins, such as urokinase. However, decontamination of negatively-charged proteins has been shown to be accompanied by a substantial loss of the product due to adsorption. For small proteins, such as myoglobin (Mw~18 kDa), ultrafiltration can be useful to remove large endotoxin aggregates. However, for large proteins, such as immunoglobulins (Mw~150 kDa) ultrafiltration has been shown not to be effective. Thus, for polyanionic polymer-conjugates with high molecular weights (Mw>20 kDa) neither ultrafiltration nor anionic-exchange chromatography are suitable. Therefore, a simple, scalable and cost-effective endotoxin-removal procedure is needed to lower the endotoxin content in large polyanionic polymer-conjugates, such as PGGA-polymer conjugates and PGA-polymer conjugates.

As described herein endotoxin levels can be reduced from a starting polyanionic polymer conjugate to suitable levels for pharmaceutical use utilizing acid precipitation of the polymer conjugate, selective dissolution and washing away of endotoxins with a solvent mixture.

Methods of purifying polyanionic polymer conjugate by lowering the endotoxin levels can include combining a starting polyanionic polymer conjugate with a first solvent system to form a solution; precipitating a portion of the starting polyanionic polymer conjugate by lowering the pH of the solution; and washing the precipitated polyanionic polymer conjugate with a second solvent system to provide a purified polyanionic polymer conjugate, wherein the amount of endotoxin present in the purified polyanionic polymer conjugate is less than the amount of endotoxin present in the starting polyanionic polymer conjugate. In some embodiments, the starting polyanionic-polymer conjugate and the purified polyanionic polymer conjugate can be a polyanionic anticancer drug conjugate. In some embodiments, the first solvent system includes a water miscible organic solvent. In some embodiments, the second solvent system includes a water miscible organic solvent.

In some embodiments, the polyanionic polymer conjugate described herein can be a PGGA-polymer conjugate. In some embodiments, the PGGA-polymer conjugate described herein can be a PGGA-anticancer drug conjugate, such as those PGGA-anticancer drug conjugates described herein. In some embodiments, a method of purifying a PGGA-anticancer drug conjugate can include combining a starting PGGA-anticancer drug conjugate with a first solvent system to form a solution; precipitating a portion of the starting PGGA-anticancer drug conjugate by lowering the pH of the solution; and washing the precipitated PGGA-anticancer drug conjugate with a second solvent system to provide a purified PGGA-anticancer drug conjugate, wherein the amount of endotoxin present in the purified PGGA-anticancer drug conjugate is less than the amount of endotoxin present in the starting PGGA-anticancer drug conjugate.

In some embodiments, the polyanionic polymer conjugate described herein can be a PGA-polymer conjugate. In some embodiments, the PGA-polymer conjugate described herein can be a PGA-anticancer drug conjugate, such as PGA-PTX. In some embodiments, a method of purifying a PGA-polymer conjugate can include combining a starting PGA-polymer conjugate with a first solvent system to form a solution; precipitating a portion of the starting PGA-polymer conjugate by lowering the pH of the solution; and washing the precipitated PGA-polymer conjugate with a second solvent system to provide a purified PGA-polymer conjugate, wherein the amount of endotoxin present in the purified PGA-polymer conjugate is less than the amount of endotoxin present in the starting PGA-polymer conjugate.

In other embodiments, the polyanionic polymer conjugate described herein can be a PGAA-polymer conjugate. In other embodiments, the PGAA-polymer conjugate described herein can be a PGAA-anticancer drug conjugate, such as PGAA-PTX. In some embodiments, a method of purifying a PGAA-polymer conjugate can include combining a starting PGAA-polymer conjugate with a first solvent system to form a solution; precipitating a portion of the starting PGAA-polymer conjugate by lowering the pH of the solution; and washing the precipitated PGAA-polymer conjugate with a second solvent system to provide a purified PGAA-polymer conjugate, wherein the amount of endotoxin present in the purified PGAA-polymer conjugate is less than the amount of endotoxin present in the starting PGAA-polymer conjugate.

In still other embodiments, the polyanionic polymer conjugate described herein can be a PA-polymer conjugate. In still other embodiments, the PA-polymer conjugate described herein can be a PA-anticancer drug conjugate, such as PA-PTX. In some embodiments, a method of purifying a PGA-polymer conjugate can include combining a starting PA-polymer conjugate with a first solvent system to form a solution; precipitating a portion of the starting PA-polymer conjugate by lowering the pH of the solution; and washing the precipitated PA-polymer conjugate with a second solvent system to provide a purified PA-polymer conjugate, wherein the amount of endotoxin present in the purified PA-polymer conjugate is less than the amount of endotoxin present in the starting PA-polymer conjugate.

Methods of purifying a polyanionic polymer conjugate described herein can provide a purified polymer conjugate with a lower endotoxin level compared to the endotoxin level present in the starting polymer conjugate. In some embodiments, the endotoxin level in the purified polymer conjugate can be low enough such that the purified polymer conjugate is acceptable for use in a pharmaceutical product. In some embodiments, the amount of endotoxin present in the purified polyanionic polymer conjugate (for example, poly(L-γ-glutamyl-glutamate)-anticancer drug conjugate) can be less than about 0.25 EU/mg. In some embodiments, the amount of endotoxin present in the purified polyanionic polymer conjugate can be less than about 0.15 EU/mg. In other embodiments, the amount of endotoxin present in the purified polyanionic polymer conjugate can be less than about 0.10 EU/mg. In other embodiments, the amount of endotoxin present in the purified polyanionic polymer conjugate can be less than about 0.05 EU/mg. In yet other embodiments, the amount of endotoxin present in the purified polyanionic polymer conjugate (for example, poly(L-γ-glutamyl-glutamate)-anticancer drug conjugate) can be less than about 0.01 EU/mg. Methods for measuring endotoxin content are known to those skilled in the art. One example is the limulus amebocyte lysate (LAL) assay. In some embodiments, including those of this paragraph, the amount of endotoxins present in the starting polyanionic polymer conjugate and the purified polyanionic polymer conjugate can be measured using the LAL assay.

Methods of purifying a polyanionic polymer conjugate described herein can reduce an endotoxin amount by several folds. In some embodiments, the amount of endotoxin can be reduced by at least 10 fold. In other embodiments, the amount of endotoxin can be reduced in the range of about 100 fold to about 10 fold. In yet other embodiments, the amount of endotoxin can be reduced in the range of about 100 fold to about 200 fold. In still other embodiments, the amount of endotoxin can be further reduced in the range of about 200 fold to about 500 fold.

The first solvent system that can be combined with a starting polyanionic polymer conjugate (for example PGGA-polymer conjugate or PGA-polymer conjugate described herein) can include one or more solvents. In some embodiments, the first solvent system can be a single solvent. In other embodiments, the first solvent system can be a mixture of two or more solvents. In some embodiments, the first solvent system can include water. In some embodiments, the first solvent system can be water. In some embodiments, the first solvent system can include a water miscible organic solvent. In some embodiments, the first solvent system can be a water miscible organic solvent. In some embodiments, the first solvent system can include a mixture of water and at least one water miscible organic solvent. In some embodiments, the first solvent system can be a mixture of water and at least one water miscible organic solvent. In other embodiments, the first solvent system can include a mixture of water and two or more water miscible organic solvents. In yet other embodiments, the first solvent system can include a mixture of water and ethanol. In some embodiments, the first solvent system cannot include a chlorinated solvent, for example, chloroform and/or dichloromethane.

When the first solvent system includes two or more solvents, the solvents can be present at various ratios. For example, the first solvent system can be water and ethanol present at an approximate one to one ratio. In other embodiments, the first solvent system can have two solvents present in a ratio of about 2 to about 1. In some embodiments, the first solvent system can have two solvents present in a ratio in the range of about 1 to about 1 to about 4 to about 1.

When the first solvent system includes two or more solvents, the solvents can be added to the starting polymer conjugate approximately simultaneously or at different times. For example, water can be completely added to a starting polyanionic polymer conjugate and then a water miscible organic solvent(s) (for example, ethanol) can be added. Alternatively, water and a water miscible organic solvent(s) can be added to a starting polyanionic polymer conjugate concurrently.

A variety of water-miscible solvents can be used in a method described herein. In some embodiments, the water miscible organic solvent can be selected from acetaldehyde, acetone, acetonitrile, 1,2-butanediol, 1,3-butanediol, 1,4-butanediol, 2-butoxyethanol, dimethylformamide, dimethoxyethane, dimethyl sulfoxide, 1,4-dioxane, methanol, ethanol, ethylene glycol, furfuryl alcohol, glycerol, 1-propanol, isopropanol, 1,5-pentanediol, 1,3-propanediol, propylene glycol, tetrahydrofuran and triethylene glycol. In some embodiments, the water miscible organic solvent can be ethanol.

The combining of the starting polymer conjugate with the first solvent system can be conducted at various temperatures. In some embodiments, the combining of the starting polymer conjugate with the first solvent system can be conducted at a temperature in the range of about 35° C. to about −5° C. In some embodiments, the combining of the starting polymer conjugate with the first solvent system can be conducted at a temperature in the range of about 50° C. to about −10° C.

Precipitating a portion of the starting polymer conjugate (for example, a PGGA-polymer conjugate) can be achieved by lowering the pH of the solution of the starting polymer conjugate and the first solvent system. In some embodiments, the pH of the solution can be adjusted to convert a portion of the starting polymer conjugate into its acid form. In some embodiments, the pH of the solution can be lowered to be less than about pH=2.5. In other embodiments, the pH of the solution can be lowered to be in the range of about pH=3.0 to about pH=1.5. In some embodiments, the pH of the solution can be lowered to be in the range of about pH=2.5 to about pH=1.5. By lowering the pH of the solution, the starting polyanionic polymer conjugate can be converted from its salt form to its acid form.

In its acid form, the solubility of the starting polymer conjugate in the first solvent system can decrease and a portion of the starting polyanionic polymer conjugate can precipitate out of the first solvent system. In some embodiments, the portion of the starting polymer conjugate that is precipitated can be in a range of about 40% to about 100% based on the amount of the starting polymer conjugate combined with the first solvent system. In other embodiments, the portion of the starting polymer conjugate that is precipitated can be in a range of about 60% to about 100% based on the amount of the starting polymer conjugate combined with the first solvent system. In some embodiments, the portion of the starting polymer conjugate that is precipitated can be in a range of about 80% to about 100% based on the amount of the starting polymer conjugate combined with the first solvent system. In other embodiments, the portion of the starting polymer conjugate that is precipitated can be in a range of about 90% to about 100% based on the amount of the starting polymer conjugate combined with the first solvent system. In some embodiments, the portion of the starting-polymer conjugate that is precipitated can be higher than about 60% based on the amount of the starting polymer conjugate combined with the first solvent system. In other embodiments, the portion of the starting polymer conjugate that is precipitated can be higher than about 80% based on the amount of the starting polymer conjugate combined with the first solvent system. In yet other embodiments, the portion of the starting polymer conjugate that is precipitated can be higher than about 90% based on the amount of the starting polymer conjugate combined with the first solvent system.

A variety of acids can be used to lower the pH of the solution of the starting polymer conjugate and the first solvent system. In some embodiments, the pH of the solution can be lowered using one or more acids. The acid(s) used to adjust the pH of the solution can be selected from hydrochloric acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phosphoric acid, phosphorous acid, malonic acid and any other equivalent acids known by those skilled in the art. In some embodiments, the acid can be hydrochloric acid.

Methods of purifying a polymer conjugate described herein can further include filtering the starting polyanionic polymer conjugate before lowering of the pH. In some embodiments, the starting polyanionic polymer conjugate can be filtered after addition of all the solvents of the first solvent system. In other embodiments, when the first solvent system includes two or more solvents, the starting polyanionic polymer conjugate can be filtered after the addition of at least one solvent of the first solvent system. For example, water can be combined with the starting polyanionic polymer conjugate and the resulting solution can be filtered using a method described herein. After filtration, the solution of water and the starting polyanionic polymer conjugate can be combined with a water miscible solvent (such as ethanol). In some embodiments, the filtering can be performed by using a membrane filter, a molecular sieve, filter paper, chromatography, centrifugation and combinations thereof. In some embodiments, the filtering can be performed by using a membrane filter (for example, a 0.2 μm membrane filter). In other embodiments, the filtering can be performed by chromatography. In yet other embodiments, the filtering can be performed by centrifugation.

The second solvent system for washing the precipitated polymer conjugate can include one or more solvents. The washing can be performed by a variety of methods. For example, the washing can be performed by mixing the precipitated polyanionic polymer conjugate in the second solvent system. As another example, the washing can be performed by pouring the second solvent system over the precipitated polyanionic polymer conjugate, while allowing the second solvent system to drain away from the precipitated polyanionic polymer conjugate. In some embodiments, the second solvent system can include water. In some embodiments, the second solvent system can include a water miscible organic solvent, such as ethanol. In some embodiments, the second solvent system can include a mixture of water and at least one water miscible organic solvent. In some embodiments, the second solvent system can be a mixture of water and at least one water miscible organic solvent. In some embodiments, the second solvent system can include a mixture of water and two or more water miscible organic solvents. In some embodiments, the second solvent system cannot include a chlorinated solvent, for example, chloroform and/or dichloromethane.

As with the first solvent system, when the second solvent system includes two or more solvents, the solvents can be present at various ratios. In some embodiments, the second solvent can have two solvents present in a ratio of about 1 to about 1, for example, water:ethanol at a ratio of about 1 to about 1. In other embodiments, the second solvent system can have two solvents present in a ratio of about 2 to about 1. In some embodiments, the second solvent system can have two solvents present in a ratio in the range of about 1 to about 1 to about 4 to about 1. When the second solvent system includes two or more solvents, the solvents can be added to the precipitated polymer conjugate approximately simultaneously or at different times. For example, water can be completely added to a precipitated polyanionic polymer conjugate and then a water miscible organic solvent(s) (for example, ethanol) can be added. Alternatively, water and a water miscible organic solvent(s) can be added to a precipitated polyanionic polymer conjugate concurrently.

The water miscible solvent(s) included in the second solvent system can be selected from acetaldehyde, acetone, acetonitrile, 1,2-butanediol, 1,3-butanediol, 1,4-butanediol, 2-butoxyethanol, dimethylformamide, dimethoxyethane, dimethyl sulfoxide, 1,4-dioxane, methanol, ethanol, ethylene glycol, furfuryl alcohol, glycerol, 1-propanol, isopropanol, 1,5-pentanediol, 1,3-propanediol, propylene glycol, tetrahydrofuran and triethylene glycol. In some embodiments, the water miscible solvent can be ethanol.

In some embodiments, the second solvent system can include one or more acids. The acid included in the second solvent system can be selected from hydrochloric acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phosphoric acid, phosphorous acid and malonic acid. In some embodiments, the second solvent system can include hydrochloric acid.

In some embodiments, the second solvent system can be water with an acid and a water miscible organic solvent. Suitable water miscible organic solvents and acids are described herein. In some embodiments, the second solvent system can be water with hydrochloric and ethanol.

The precipitated polymer conjugate can be washed repeatedly. In some embodiments, the precipitated polymer conjugate can be washed one or more times. In other embodiments, the precipitated polymer conjugate can be washed two or more times. In yet other embodiments, the precipitated polymer conjugate can be washed at least three times. In some embodiments, the precipitated polymer conjugate can be washed a number of times in the range of 1 to 3, 1 to 5 or 1 to 10.

When the precipitated polymer conjugate is washed multiple times, the precipitated polymer conjugate can be isolated between each washing. In some embodiments, the precipitated polymer conjugate can be isolated after at least one washing. Methods for isolating between washing are described herein and include a membrane filter, a molecular sieve, filter paper, chromatography, centrifugation and combinations thereof.

In some embodiments, when the washing is repeated at least two times, the second solvent system can be the same for at least two of the washings. In other embodiments, when the washing is repeated at least two times, the second solvent system can be different for at least two of the washings.

Methods described herein can include optionally washing the precipitated polymer conjugate with a third solvent system. As with the second solvent system, the washing with the third solvent system can be performed by various methods. In some embodiments, the washing can be performed by mixing the precipitated polyanionic polymer conjugate in the third solvent system. In other embodiments, the washing can be performed by pouring the third solvent system over the precipitated polyanionic polymer conjugate, while allowing the third solvent system to drain away from the precipitated polyanionic polymer conjugate. The third solvent system for washing the precipitated polymer conjugate can include one or more solvents. In some embodiments, the third solvent system can include water. In some embodiments, the third solvent system can include a water miscible organic solvent, such as those water miscible organic solvents described herein. In some embodiments, the third solvent system can include a mixture of water and at least one water miscible organic solvent. In some embodiments, the third solvent system can be water (for example, MilliQ water). In some embodiments, the third solvent system cannot include a chlorinated solvent, for example, chloroform and/or dichloromethane.

When the third solvent system includes two or more solvents, the solvents can be present at various ratios. The washing of the precipitated polymer conjugate with a third solvent system can occur multiple times, such as 2 or more times or 3 or more times. In some embodiments, the washing with the third solvent system can occur after the washing(s) with the second solvent system are complete. Additionally, when the third solvent system includes more than one solvent, the solvents can be added to the precipitated polymer conjugate approximately simultaneously or at different times. For example, water can be completely added to a precipitated polyanionic polymer conjugate and then a water miscible organic solvent(s) (for example, ethanol) can be added. Alternatively, water and a water miscible organic solvent(s) can be added to a precipitated polyanionic polymer conjugate concurrently.

Methods of purifying a polymer conjugate described herein can further include drying the purified polymer conjugate. A variety of drying methods can be used, and include, but are not limited to, oven drying, freeze drying, air drying and combinations thereof. In some embodiments, the purified polymer conjugate can be dried by freeze drying.

Methods of purifying a polymer conjugate described herein can include isolating the precipitated polymer conjugate after lowering the pH and before washing. Suitable methods for isolating the polymer conjugate after lowering the pH are described herein. In some embodiments, the polymer conjugate can be isolated by centrifugation.

The purified polyanionic polymer conjugate can be in its acid form or in its salt form. The alkali metal salt of the purified polyanionic polymer conjugate (for example, the sodium salt of a PGGA-polymer conjugate) can be formed using methods known to those skilled in the art. In some embodiments, the alkali metal salt of the polymer conjugate can be the sodium salt. In some embodiments, the alkali metal salt of the purified polyanionic polymer conjugate can be formed after the final washing.

Various alkali metal bases can be used to form the alkali metal salt of the polymer conjugate. Examples of suitable alkali metal base include metal bicarbonate, an alkali metal carbonate and an alkali metal hydroxide. In some embodiments, the alkali metal base can be sodium bicarbonate. In other embodiments, the alkali metal base can be sodium hydroxide. In some embodiments, the alkali metal base can be sodium carbonate.

Methods of purifying a polyanionic polymer conjugate described herein can include further purifying the alkali metal salt of the polymer conjugate obtained after the final washing. A variety of methods can be used. In some embodiments, the alkali metal salt of a polymer conjugate can be purified using a final tangential flow filtration (TFF) system. In some embodiments, the alkali metal salt of a polymer conjugate can be purified using dialysis tubing.

The alkali metal salt of the polymer conjugate can be filtered after purification if desired and/or needed. In some embodiments, the filtering can be performed by using a membrane filter, a molecular sieve, filter paper, chromatography, centrifugation and combinations thereof. In some embodiments, the filtering can be performed by using a membrane filter. In some embodiments, the filtering can be performed by using chromatography.

Polymer Conjugates

Some embodiments described herein generally relate to a method of purifying a polyanionic polymer conjugate that can include one or more recurring units of Formula (Ia) and one or more recurring units of Formula (IIa):

(Ia)

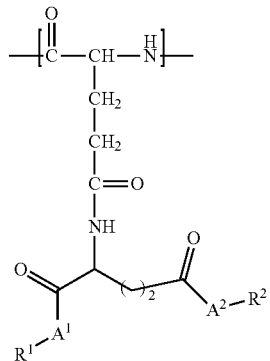

(IIa)

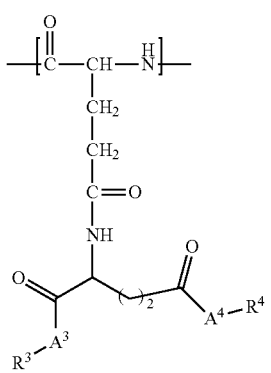

wherein: each $A^1$, each $A^2$, each $A^3$ and each $A^4$ can be independently O (oxygen) or NH; each $R^1$ and each $R^2$ can be independently hydrogen or an alkali metal; and each $R^3$ and each $R^4$ can be independently hydrogen, an alkali metal, a targeting agent, an imaging agent, a stabilizing agent or an anticancer drug, provided that at least one of $R^3$ and $R^4$ is a targeting agent, an imaging agent, a stabilizing agent or an anticancer drug, and the other of $R^3$ and $R^4$ is hydrogen or an alkali metal.

Some embodiments described herein generally relate to a method of purifying a polyanionic polymer conjugate that can include one or more recurring units of Formula (Ib) and one or more recurring units of Formula (IIb):

(Ib)

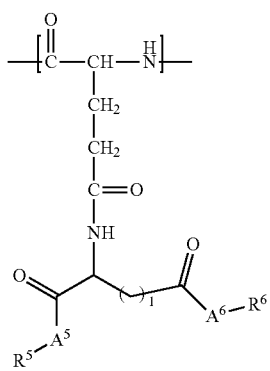

(IIb)

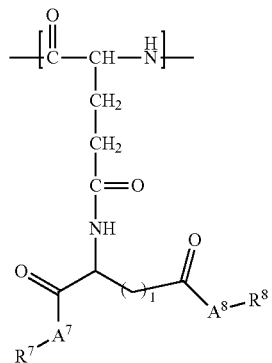

wherein: each $A^5$, each $A^6$, each $A^7$ and each $A^8$ can be independently O (oxygen) or NH; each $R^5$ and each $R^6$ can be independently hydrogen or an alkali metal; and each $R^7$ and each $R^8$ can be independently hydrogen, an alkali metal, a targeting agent, an imaging agent, a stabilizing agent or an anticancer drug, provided that at least one of $R^7$ and $R^8$ is a targeting agent, an imaging agent, a stabilizing agent or an anticancer drug, and the other of $R^7$ and $R^8$ is hydrogen or an alkali metal.

Some embodiments described herein generally relate to a method of purifying a polyanionic polymer conjugate that can include one or more recurring units of Formula (Ic) and one or more recurring units of Formula (IIc):

(Ic)

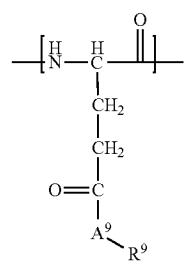

(IIc)

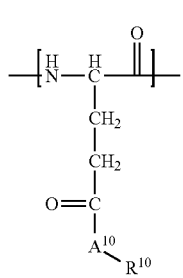

wherein: each $A^9$ and each $A^{10}$ can be independently O (oxygen) or NH; each $R^9$ can be hydrogen or an alkali metal; and each $R^{10}$ can be a targeting agent, an imaging agent, a stabilizing agent or an anticancer drug.

Some embodiments described herein generally relate to a method of purifying a polyanionic polymer conjugate that can include one or more recurring units of Formula (Id) and one or more recurring units of Formula (IId):

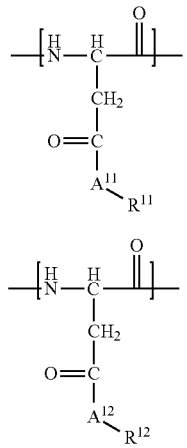

(Id)

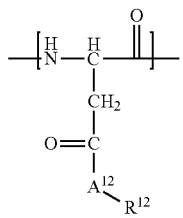

(IId)

wherein: each $A^{11}$ and each $A^{12}$ can be independently O (oxygen) or NH; each $R^{11}$ can be hydrogen or an alkali metal; and each $R^{12}$ can be a targeting agent, an imaging agent, a stabilizing agent or an anticancer drug.

Some embodiments described herein generally relate to a method of purifying a polyanionic polymer conjugate that can include one or more recurring units of Formula (Ie) and one or more recurring units of Formula (IIe):

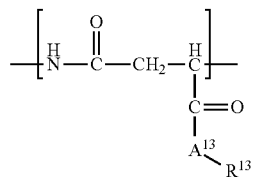

(Ie)

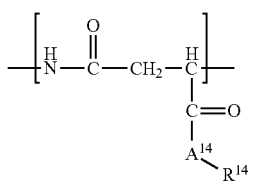

(IIe)

wherein: each $A^{13}$ and each $A^{14}$ can be independently O (oxygen) or NH; $R^{13}$ can be hydrogen or an alkali metal; and $R^{14}$ can be a targeting agent, an imaging agent, a stabilizing agent or an anticancer drug.

Some embodiments described herein generally relate to a method of purifying a polyanionic polymer conjugate that can include one or more recurring units of Formula (If) and one or more recurring units of Formula (IIf):

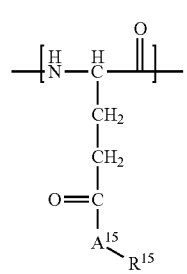

(If)

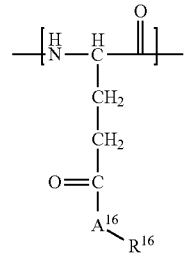

(IIf)

wherein: each $A^{15}$ and each $A^{16}$ can be independently O (oxygen) or NH; each $R^{15}$ can be hydrogen or an alkali metal; and each $R^{16}$ can be a targeting agent, an imaging agent, a stabilizing agent or an anticancer drug. Those skilled in the art understand that when an alkali metal is present and $A^1, A^2, A^3, A^4, A^5, A^6, A^7, A^8, A^9, A^{10}, A^{11}, A^{12}, A^{13}, A^{14}, A^{15}$ or $A^{16}$ are oxygen, the oxygen will have a negative charge, the alkali metal will have a positive charge, and the bond between the oxygen and the alkali metal will be an electrostatic bond.

Some embodiments described herein generally relate to a method of purifying a polyanionic polymer conjugate wherein the polyanionic polymer conjugate can be a copolymer conjugate. A copolymer conjugate can include a broad variety of at least two different types of recurring units. For example, a copolymer conjugate can include one or more recurring units selected from Formulae (Ia), (Ib), (Ic), (Ic), (Ie) and (If); and one or more recurring units of Formulae (IIa), (IIb), (IIc), (IIc), (IIe) and (IIf), provided that the polymer is not only recurring units of (Ia) and (IIa); (Ib) and (IIb); (Ic) and (IIc); (Id) and (IId); (Ie) and (IIe); (If) and (IIf); (Id), (IId), (Ie) and (IIe); (Ic), (IIc), (If) and (IIf).

In some embodiments, the polymer conjugate can be a copolymer conjugate that can include recurring units of Formula (Ia), recurring units of Formula (Ib) and recurring units of at least one of Formula (IIa) and Formula (IIb). In other embodiments, the polymer conjugate can be a copolymer conjugate that can include the recurring units of Formula (Ia), recurring units of Formula (Ic) and recurring units of at least one of Formula (IIa) and Formula (IIc). In still other embodiments, the polymer conjugate can be a copolymer conjugate that can include the recurring units of Formula (Ia), recurring units of Formula (Id) and recurring units of at least one of Formula (IIa) and Formula (IId). In yet still embodiments, the polymer conjugate can be a copolymer conjugate that can include the recurring units of Formula (Ia), recurring units of Formula (Ie) and recurring units of at least one of Formula (IIa) and Formula (IIe). In some embodiments, the polymer conjugate can be a copolymer conjugate that can include the recurring units of Formula (Ia), recurring units of Formula (If) and recurring units of at least one of Formula (IIa) and Formula (IIf).

In some embodiments, the polymer conjugate can be a copolymer conjugate that can include recurring units of Formula (Ib), recurring units of Formula (Id) and recurring units of at least one of Formula (IIb) and Formula (IId). In other embodiments, the polymer conjugate can be a copolymer can include recurring units of Formula (Ib) and recurring units of Formula (Ic), and recurring units of at least one of Formula (IIb) and Formula (IIc). In still other embodiments, the polymer conjugate can be a copolymer can include recurring units of Formula (Ib) and recurring units of Formula (Id), and recurring units of at least one of Formula (IIb) and Formula (IId). In yet other embodiments, the polymer conjugate can be a copolymer can include recurring units of Formula (Ib) and recurring units of Formula (Ie), and recurring units of at least one of Formula (IIb) and Formula (IIe). In some embodiments, the polymer conjugate can be a copolymer can include recurring units of Formula (Ib) and recurring units of Formula (If), and recurring units of at least one of Formula (IIb) and Formula (IIf).

In some embodiments, the polymer conjugate can be a copolymer conjugate that can include recurring units of Formula (Ic) and recurring units of Formula (Id) and recurring units of at least one of Formula (IIc) and Formula (IId). In other embodiments, the polymer conjugate can be a copolymer conjugate that can include recurring units of Formula (Ic) and recurring units of Formula (Ie) and recurring units of at least one of Formula (IIc) and Formula (IIe). In some embodiments, the polymer conjugate can be a copolymer conjugate that can include recurring units of Formula (Id) and recurring units of Formula (If) and recurring units of at least one of Formula (IId) and Formula (IIf). In other embodiments, the polymer conjugate can be a copolymer conjugate that can include recurring units of Formula (Ie) and recurring units of Formula (If) and recurring units of at least one of Formula (IIe) and Formula (IIf).

In some embodiments, the polymer conjugate can be a copolymer conjugate that can include recurring units of Formula (Ia), recurring units of Formula (Ib), recurring units of Formula (Ic) and recurring units of at least one of Formula (IIa), Formula (IIb) and Formula (IIc). In other embodiments, the polymer conjugate can be a copolymer conjugate that can include recurring units of Formula (Ia), recurring units of Formula (Ib), recurring units of Formula (Id) and recurring units of at least one of Formula (IIa), Formula (IIb) and Formula (IId). In still other embodiments, the polymer conjugate can be a copolymer conjugate that can include recurring units of Formula (Ia), recurring units of Formula (Ib), recurring units of Formula (Ie) and recurring units of at least one of Formula (IIa), Formula (IIb) and Formula (IIe). In yet still other embodiments, the polymer conjugate can be a copolymer conjugate that can include recurring units of Formula (Ia), recurring units of Formula (Ib), recurring units of Formula (If) and recurring units of at least one of Formula (IIa), Formula (IIb) and Formula (IIf).

In some embodiments, the polymer conjugate can be a copolymer conjugate that can include recurring units of Formula (Ib), recurring units of Formula (Ic), recurring units of Formula (Id) and recurring units of at least one of Formula (IIb), Formula (IIc) and Formula (IId). In other embodiments, the polymer conjugate can be a copolymer conjugate that can include recurring units of Formula (Ib), recurring units of Formula (Ic), recurring units of Formula (Ie) and recurring units of at least one of Formula (IIb), Formula (IIc) and Formula (IIe). In still other embodiments, the polymer conjugate can be a copolymer conjugate that can include recurring units of Formula (Ib), recurring units of Formula (Ic), recurring units of Formula (If) and recurring units of at least one of Formula (IIb), Formula (IIc) and Formula (IIf).

In some embodiments, the polymer conjugate can be a copolymer conjugate that can include recurring units of Formula (Ic), recurring units of Formula (Id), recurring units of Formula (Ie) and recurring units of at least one of Formula (IIc), Formula (IId) and Formula (IIe). In other embodiments, the polymer conjugate can be a copolymer conjugate that can include recurring units of Formula (Ic), recurring units of Formula (Id), recurring units of Formula (If) and recurring units of at least one of Formula (IIc), Formula (IId) and Formula (IIf). In some embodiments, the polymer conjugate can be a copolymer conjugate that can include recurring units of Formula (Id), recurring units of Formula (Ie), recurring units of Formula (If) and recurring units of at least one of Formula (IId), Formula (IIe) and Formula (IIf).

In some embodiments, the polymer conjugate can be a copolymer conjugate that can include recurring units of Formula (Ia), recurring units of Formula (Ib), recurring units of Formula (Ic), recurring units of Formula (Id) and recurring units of at least one of Formula (IIa), Formula (IIb), Formula (IIc) and Formula (IId). In other embodiments, the polymer conjugate can be a copolymer conjugate that can include recurring units of Formula (Ia), recurring units of Formula (Ib), recurring units of Formula (Ic), recurring units of Formula (Ie) and recurring units of at least one of Formula (IIa), Formula (IIb), Formula (IIc) and Formula (IIe). In still other embodiments, the polymer conjugate can be a copolymer conjugate that can include recurring units of Formula (Ia), recurring units of Formula (Ib), recurring units of Formula (Ic), recurring units of Formula (If) and recurring units of at least one of Formula (IIa), Formula (IIb), Formula (IIc) and Formula (IIf).

In some embodiments, the polymer conjugate can be a copolymer conjugate that can include recurring units of Formula (Ib), recurring units of Formula (Ic), recurring units of Formula (Id), recurring units of Formula (Ie) and recurring units of at least one of Formula (IIb), Formula (IIc), Formula (IId) and Formula (IIe). In other embodiments, the polymer conjugate can be a copolymer conjugate that can include recurring units of Formula (Ib), recurring units of Formula (Ic), recurring units of Formula (Id), recurring units of Formula (If) and recurring units of at least one of Formula (IIb), Formula (IIc), Formula (IId) and Formula (IIf). In some embodiments, the polymer conjugate can be a copolymer conjugate that can include recurring units of Formula (Ic), recurring units of Formula (Id), recurring units of Formula (Ie), recurring units of Formula (If) and recurring units of at least one of Formula (IIc), Formula (IId), Formula (IIe) and Formula (IIf).

In some embodiments, the polymer conjugate can be a copolymer conjugate that can include recurring units of Formula (Ia), recurring units of Formula (Ib), recurring units of Formula (Ic), recurring units of Formula (Id), recurring units of Formula (Ie) and recurring units of at least one of Formula (IIa), Formula (IIb), Formula (IIc), Formula (IId) and Formula (IIe). In other embodiments, the polymer conjugate can be a copolymer conjugate that can include recurring units of Formula (Ia), recurring units of Formula (Ib), recurring units of Formula (Ic), recurring units of Formula (Id), recurring units of Formula (If) and recurring units of at least one of Formula (IIa), Formula (IIb), Formula (IIc), Formula (IId) and Formula (IIf). In some embodiments, the polymer conjugate can be a copolymer conjugate that can include recurring units of Formula (Ib), recurring units of Formula (Id), recurring units of Formula (Id), recurring units of Formula (Ie), recurring units of Formula (If) and recurring units of at least one of Formula (IIb), Formula (IIc), Formula (IId), Formula (IIe) and Formula (IIf).

In some embodiments, the polymer conjugate can be a copolymer conjugate that can include recurring units of Formula (Ia), recurring units of Formula (Ib), recurring units of Formula (Id), recurring units of Formula (Id), recurring units of Formula (Ie), recurring units of Formula (If) and recurring units of at least one of Formula (IIa), Formula (IIb), Formula (IIc), Formula (IId), Formula (IIe) and Formula (IIf).

The percentage of recurring units in a polyanionic polymer conjugate, based on the total number of recurring units, may vary over a wide range. In some embodiments, the percentage of recurring units Formula (Ia) and recurring units of Formula (IIa) can be in the range of about 50 mole % to about 99 mole % based on the total moles of recurring units in the polymer conjugate. In some embodiments, the percentage of recurring units Formula (Ia) and recurring units of Formula (IIa) can be in the range of about 80 mole % to about 99 mole % based on the total moles of recurring units in the polymer conjugate. In other embodiments, the percentage of recurring units Formula (Ia) and recurring units of Formula (IIa) can be in the range of about 90 mole % to about 99 mole % based on the total moles of recurring units in the polymer conjugate. In still other embodiments, the percentage of recurring units Formula (Ia) and recurring units of Formula (IIa) can be in the range of about 95 mole % to about 99 mole % based on the total moles of recurring units in the polymer conjugate. In yet still other embodiments, the percentage of recurring units Formula (Ia) and recurring units of Formula (IIa) can be greater than about 99 mole % based on the total moles of recurring units in the polymer conjugate. In some embodiments, the percentage of recurring units Formula (Ia) and recurring units of Formula (IIa) can be in the range of about 20 mole % to about 40 mole % based on the total moles of recurring units in the polymer conjugate. In other embodiments, the percentage of recurring units Formula (Ia) and recurring units of Formula (IIa) can be in the range of about 30 mole % to about 60 mole % based on the total moles of recurring units in the polymer conjugate. In some embodiments, the polymer conjugate can consists of, or consists essentially of recurring units of Formula (Ia) and recurring units of Formula (IIa). When the polyanionic polymer conjugate is a copolymer conjugate, in some embodiments, the recurring units that are not of Formulae (Ia) or (IIa) can be selected from Formulae (Ib), (IIb), (Ic), (IIc), (Id), (IId), (Ie), (IIe), (If) and (IIf) such that the polymer conjugate can consist of, or consist essentially of recurring units of Formulae (Ia) and (IIa) and recurring units selected from Formulae (Ib), (IIb), (Ic), (IIc), (Id), (IId), (Ie), (IIe), (If) and (IIf).

In some embodiments, the percentage of recurring units Formula (Ib) and recurring units of Formula (IIb) can be in the range of about 50 mole % to about 99 mole % based on the total moles of recurring units in the polymer conjugate. In some embodiments, the percentage of recurring units Formula (Ib) and recurring units of Formula (IIb) can be in the range of about 80 mole % to about 99 mole % based on the total moles of recurring units in the polymer conjugate. In other embodiments, the percentage of recurring units Formula (Ib) and recurring units of Formula (IIb) can be in the range of about 90 mole % to about 99 mole % based on the total moles of recurring units in the polymer conjugate. In still other embodiments, the percentage of recurring units Formula (Ib) and recurring units of Formula (IIb) can be in the range of about 95 mole % to about 99 mole % based on the total moles of recurring units in the polymer conjugate. In yet still other embodiments, the percentage of recurring units Formula (Ib) and recurring units of Formula (IIb) can be greater than about 99 mole % based on the total moles of recurring units in the polymer conjugate. In some embodiments, the percentage of recurring units Formula (Ib) and recurring units of Formula (IIb) can be in the range of about 20 mole % to about 40 mole % based on the total moles of recurring units in the polymer conjugate. In other embodiments, the percentage of recurring units Formula (Ib) and recurring units of Formula (IIb) can be in the range of about 30 mole % to about 60 mole % based on the total moles of recurring units in the polymer conjugate. In some embodiments, the polymer conjugate can consists of, or consists essentially of recurring units of Formula (Ib) and recurring units of Formula (IIb). When the polyanionic polymer conjugate is a copolymer conjugate, in some embodiments, the recurring units that are not of Formulae (Ib) or (IIb) can be selected from Formulae (Ia), (IIa), (Ic), (IIc), (Id), (IId), (Ie), (IIe), (If) and (IIf) such that the polymer conjugate can consist of, or consist essentially of recurring units of Formulae (Ib) and (IIb) and recurring units selected from Formulae (Ia), (IIa), (Ic), (IIc), (Id), (IId), (Ie), (IIe), (If) and (IIf).

In some embodiments, the percentage of recurring units Formula (Ic) and recurring units of Formula (IIc) can be in the range of about 50 mole % to about 99 mole % based on the total moles of recurring units in the polymer conjugate. In some embodiments, the percentage of recurring units Formula (Ic) and recurring units of Formula (IIc) can be in the range of about 80 mole % to about 99 mole % based on the total moles of recurring units in the polymer conjugate. In other embodiments, the percentage of recurring units Formula (Ic) and recurring units of Formula (IIc) can be in the range of about 90 mole % to about 99 mole % based on the total moles of recurring units in the polymer conjugate. In still other embodiments, the percentage of recurring units Formula (Ic) and recurring units of Formula (IIc) can be in the range of about 95 mole % to about 99 mole % based on the total moles of recurring units in the polymer conjugate. In yet still other embodiments, the percentage of recurring units Formula (Ic) and recurring units of Formula (IIc) can be greater than about 99 mole % based on the total moles of recurring units in the polymer conjugate. In some embodiments, the polymer conjugate can consist of recurring units of Formula (Ic) and recurring units of Formula (IIc). In some embodiments, the percentage of recurring units Formula (Ic) and recurring units of Formula (IIc) can be in the range of about 20 mole % to about 40 mole % based on the total moles of recurring units in the polymer conjugate. In other embodiments, the percentage of recurring units Formula (Ic) and recurring units of Formula (IIc) can be in the range of about 30 mole % to about 60 mole % based on the total moles of recurring units in the polymer conjugate. In some embodiments, the polymer conjugate can consists of, or consists essentially of recurring units of Formula (Ic) and recurring units of Formula (IIc). When the polyanionic polymer conjugate is a copolymer conjugate, in some embodiments, the recurring units that are not of Formulae (Ic) or (IIc) can be selected from Formulae (Ia), (IIa), (Ib), (IIb), (Id), (IId), (Ie), (IIe), (If) and (IIf) such that the polymer conjugate can consist of, or consist essentially of recurring units of Formulae (Ic) and (IIc) and recurring units selected from Formulae (Ia), (IIa), (Ib), (IIb), (Id), (IId), (Ie), (IIe), (If) and (IIf).

In some embodiments, the percentage of recurring units Formula (Id) and recurring units of Formula (IId) can be in the range of about 50 mole % to about 99 mole % based on the total moles of recurring units in the polymer conjugate. In some embodiments, the percentage of recurring units Formula (Id) and recurring units of Formula (IId) can be in the range of about 80 mole % to about 99 mole % based on the total moles of recurring units in the polymer conjugate. In other embodiments, the percentage of recurring units Formula (Id) and recurring units of Formula (IId) can be in the range of about 90 mole % to about 99 mole % based on the total moles of recurring units in the polymer conjugate. In still other embodiments, the percentage of recurring units Formula (Id) and recurring units of Formula (IId) can be in the range of about 95 mole % to about 99 mole % based on the total moles of recurring units in the polymer conjugate. In yet still other embodiments, the percentage of recurring units Formula (Id) and recurring units of Formula (IId) can be greater than about 99 mole % based on the total moles of recurring units in the polymer conjugate. In some embodiments, the polymer conjugate can consist of recurring units of Formula (Id) and recurring units of Formula (IId). In some embodiments, the percentage of recurring units Formula (Id) and recurring units of Formula (IId) can be in the range of about 20 mole % to about 40 mole % based on the total moles of recurring units in the polymer conjugate. In other embodiments, the percentage of recurring units Formula (Id) and recurring units of Formula (IId) can be in the range of about 30 mole % to about 60 mole % based on the total moles of recurring units in the polymer conjugate. In some embodiments, the polymer conjugate can consists of, or consists essentially of recurring units of Formula (Id) and recurring units of Formula (IId). When the polyanionic polymer conjugate is a copolymer conjugate, in some embodiments, the recurring units that are not of Formulae (Id) or (IId) can be selected from Formulae (Ia), (IIa), (Ib), (IIb), (Ic), (IIc), (Ie), (IIe), (If) and (IIf) such that the polymer conjugate can consist of, or consist essentially of recurring units of Formulae (Id) and (IId) and recurring units selected from Formulae (Ia), (IIa), (Ib), (IIb), (Ic), (IIc), (Ie), (IIe), (If) and (IIf).

In some embodiments, the percentage of recurring units Formula (Ie) and recurring units of Formula (IIe) can be in the range of about 50 mole % to about 99 mole % based on the total moles of recurring units in the polymer conjugate. In some embodiments, the percentage of recurring units Formula (Ie) and recurring units of Formula (IIe) can be in the range of about 80 mole % to about 99 mole % based on the total moles of recurring units in the polymer conjugate. In other embodiments, the percentage of recurring units Formula (Ie) and recurring units of Formula (IIe) can be in the range of about 90 mole % to about 99 mole % based on the total moles of recurring units in the polymer conjugate. In still other embodiments, the percentage of recurring units Formula (Ie) and recurring units of Formula (IIe) can be in the range of about 95 mole % to about 99 mole % based on the total moles of recurring units in the polymer conjugate. In yet still other embodiments, the percentage of recurring units Formula (Ie) and recurring units of Formula (IIe) can be greater than about 99 mole % based on the total moles of recurring units in the polymer conjugate. In some embodiments, the polymer conjugate can consist of recurring units of Formula (Ie) and recurring units of Formula (IIe). In some embodiments, the percentage of recurring units Formula (Ie) and recurring units of Formula (IIe) can be in the range of about 20 mole % to about 40 mole % based on the total moles of recurring units in the polymer conjugate. In other embodiments, the percentage of recurring units Formula (Ie) and recurring units of Formula (IIe) can be in the range of about 30 mole % to about 60 mole % based on the total moles of recurring units in the polymer conjugate. In some embodiments, the polymer conjugate can consists of, or consists essentially of recurring units of Formula (Ie) and recurring units of Formula (IIe). When the polyanionic polymer conjugate is a copolymer conjugate, in some embodiments, the recurring units that are not of Formulae (Ie) or (IIe) can be selected from Formulae (Ia), (IIa), (Ib), (IIb), (Ic), (IIc), (Id), (IId), (If) and (IIf) such that the polymer conjugate can consist of, or consist essentially of recurring units of Formulae (Ie) and (IIe) and recurring units selected from Formulae (Ia), (IIa), (Ib), (IIb), (Ic), (IIc), (Id), (IId), (If) and (IIf).

In some embodiments, the percentage of recurring units Formula (If) and recurring units of Formula (IIf) can be in the range of about 50 mole % to about 99 mole % based on the total moles of recurring units in the polymer conjugate. In some embodiments, the percentage of recurring units Formula (If) and recurring units of Formula (IIf) can be in the range of about 80 mole % to about 99 mole % based on the total moles of recurring units in the polymer conjugate. In other embodiments, the percentage of recurring units Formula (If) and recurring units of Formula (IIf) can be in the range of about 90 mole % to about 99 mole % based on the total moles of recurring units in the polymer conjugate. In still other embodiments, the percentage of recurring units Formula (If) and recurring units of Formula (IIf) can be in the range of about 95 mole % to about 99 mole % based on the total moles of recurring units in the polymer conjugate. In yet still other embodiments, the percentage of recurring units Formula (If) and recurring units of Formula (IIf) can be greater than about 99 mole % based on the total moles of recurring units in the polymer conjugate. In some embodiments, the polymer conjugate can consist of recurring units of Formula (If) and recurring units of Formula (IIf). In some embodiments, the percentage of recurring units Formula (If) and recurring units of Formula (IIf) can be in the range of about 20 mole % to about 40 mole % based on the total moles of recurring units in the polymer conjugate. In other embodiments, the percentage of recurring units Formula (If) and recurring units of Formula (IIf) can be in the range of about 30 mole % to about 60 mole % based on the total moles of recurring units in the polymer conjugate. In some embodiments, the polymer conjugate can consists of, or consists essentially of recurring units of Formula (If) and recurring units of Formula (IIf). When the polyanionic polymer conjugate is a copolymer conjugate, in some embodiments, the recurring units that are not of Formulae (If) or (IIf) can be selected from Formulae (Ia), (IIa), (Ib), (IIb), (Ic), (IIc), (Id), (IId), (Ie) and (IIe) such that the polymer conjugate can consist of, or consist essentially of recurring units of Formulae (If) and (IIf) and recurring units selected from Formulae (Ia), (IIa), (Ib), (IIb), (Ic), (IIc), (Id), (IId), (Ie) and (IIe).

In some embodiments, a polymer conjugate described herein can include an alkali metal. Examples of alkali metals include lithium (Li), sodium (Na), potassium (K), rubidium (Rb), and cesium (Cs). In some embodiments, the alkali metal can be sodium.

A polyanionic polymer conjugate described herein (for example, a polymer conjugate that includes recurring units of Formula (Ia) and recurring units of Formula (IIa)) can be in its acid form or in its alkali metal salt form. In some embodiments, the polymer conjugate can be in the acid form. In other embodiments, the polymer conjugate can be in the alkali metal salt form. As example, the acid form and alkali metal salt form of a polymer that includes recurring units of Formula (Ia) and recurring units of Formula (IIa) are shown below.

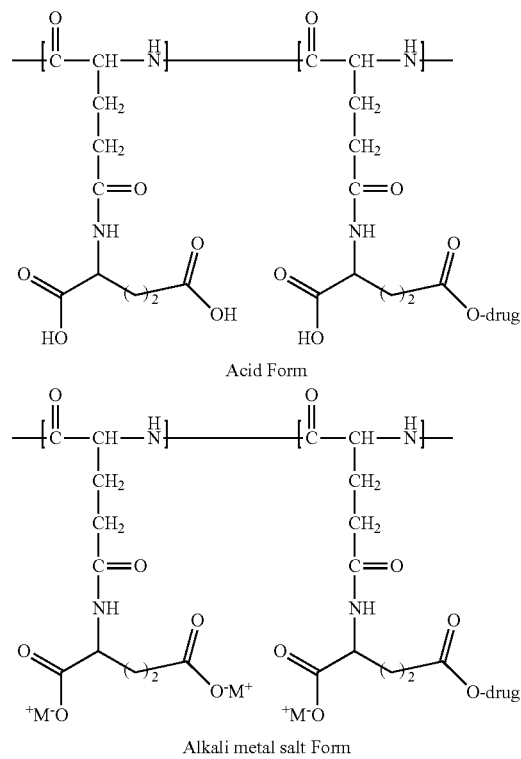

M = alkali metal base

In some embodiments, at least 90% of $R^1$ and $R^2$ can be hydrogen and at least 90% of $R^3$ and $R^4$ that are not an anticancer drug can be hydrogen. In some embodiments, at least 95% of $R^1$ and $R^2$ can be hydrogen and at least 95% of $R^3$ and $R^4$ that are not an anticancer drug can be hydrogen. In some embodiments, greater than 98% of $R^1$ and $R^2$ can be hydrogen and greater than 98% of $R^3$ and $R^4$ that are not an anticancer drug can be hydrogen. In other embodiments, at least 90% of $R^1$ and $R^2$ can be an alkali metal and at least 90% of $R^3$ and $R^4$ that are not an anticancer drug can be an alkali metal. In other embodiments, at least 95% of $R^1$ and $R^2$ can be an alkali metal and at least 95% of $R^3$ and $R^4$ that are not an anticancer drug can be an alkali metal. In other embodiments, greater than 98% of $R^1$ and $R^2$ can be an alkali metal and greater than 98% of $R^3$ and $R^4$ that are not an anticancer drug can be an alkali metal.

In some embodiments, at least 90% of $R^5$ and $R^6$ can be hydrogen and at least 90% of $R^7$ and $R^8$ that are not an anticancer drug can be hydrogen. In some embodiments, at least 95% of $R^5$ and $R^6$ can be hydrogen and at least 95% of $R^7$ and $R^8$ that are not an anticancer drug can be hydrogen. In some embodiments, greater than 98% of $R^5$ and $R^6$ can be hydrogen and greater than 98% of $R^7$ and $R^8$ that are not an anticancer drug can be hydrogen. In other embodiments, at least 90% of $R^5$ and $R^6$ can be an alkali metal and at least 90% of $R^7$ and $R^8$ that are not an anticancer drug can be an alkali metal. In other embodiments, at least 95% of $R^5$ and $R^6$ can be an alkali metal and at least 95% of $R^7$ and $R^8$ that are not an anticancer drug can be an alkali metal. In other embodiments, greater than 98% of $R^5$ and $R^6$ can be an alkali metal and greater than 98% of $R^7$ and $R^8$ that are not an anticancer drug can be an alkali metal.

In some embodiments, at least 90% of $R^9$ can be hydrogen. In some embodiments, at least 95% of $R^9$ can be hydrogen. In some embodiments, greater than 98% of $R^9$ can be hydrogen. In other embodiments, at least 90% of $R^9$ can be an alkali metal. In other embodiments, at least 95% of $R^9$ can be an alkali metal. In other embodiments, greater than 98% of $R^9$ can be an alkali metal.

In some embodiments, at least 90% of $R^{11}$ can be hydrogen. In some embodiments, at least 95% of $R^{11}$ can be hydrogen. In some embodiments, greater than 98% of $R^{11}$ can be hydrogen. In other embodiments, at least 90% of $R^{11}$ can be an alkali metal. In other embodiments, at least 95% of $R^{11}$ can be an alkali metal. In other embodiments, greater than 98% of $R^{11}$ can be an alkali metal.

In some embodiments, at least 90% of $R^{13}$ can be hydrogen. In some embodiments, at least 95% of $R^{13}$ can be hydrogen. In some embodiments, greater than 98% of $R^{13}$ can be hydrogen. In other embodiments, at least 90% of $R^{13}$ can be an alkali metal. In other embodiments, at least 95% of $R^{13}$ can be an alkali metal. In other embodiments, greater than 98% of $R^{13}$ can be an alkali metal.

In some embodiments, at least 90% of $R^{15}$ can be hydrogen. In some embodiments, at least 95% of $R^{15}$ can be hydrogen. In some embodiments, greater than 98% of $R^{15}$ can be hydrogen. In other embodiments, at least 90% of $R^{15}$ can be an alkali metal. In other embodiments, at least 95% of $R^{15}$ can be an alkali metal. In other embodiments, greater than 98% of $R^{15}$ can be an alkali metal.

A variety of anticancer drugs can be attached to a polymer to form a polyanionic anticancer drug conjugate. In some embodiments, the anticancer drug can be selected from a taxane, a camptotheca, and an anthracycline. In some embodiments, the camptotheca can be camptothecin. In some embodiments, the anthracycline can be doxorubicin. Examples of taxanes include, but are not limited to, paclitaxel and docetaxel. In some embodiments, the taxane can be paclitaxel. When the anticancer drug is paclitaxel, the paclitaxel can be attached to a recurring unit at the oxygen atom attached to the C2'-carbon of paclitaxel or the oxygen atom attached to the C7-carbon of paclitaxel.

The amount of targeting agent, imaging agent, stabilizing agent or anticancer drug present in the polyanionic polymer conjugate (such as, a PGGA polymer conjugate or a PGA polymer conjugate) can vary over a wide range. In some embodiments, the polymer conjugate can include a total amount of targeting agent, imaging agent, stabilizing agent or anticancer drug in the range of about 5% to about 50% (weight/weight) based on the mass ratio of targeting agent, imaging agent, stabilizing agent or anticancer drug to the polymer conjugate. In other embodiments, the polymer conjugate can include a total amount of targeting agent, imaging agent, stabilizing agent or anticancer drug in the range of about 10% to about 40% (weight/weight) based on the mass ratio of targeting agent, imaging agent, stabilizing agent or anticancer drug to the polymer conjugate. In still other embodiments, the polymer conjugate can include a total amount of targeting agent, imaging agent, stabilizing agent or anticancer drug in the range of about 20% to about 40% (weight/weight) based on the mass ratio of targeting agent, imaging agent, stabilizing agent or anticancer drug to the polymer conjugate. In yet still other embodiments, the polymer conjugate can include a total amount of targeting agent, imaging agent, stabilizing agent or anticancer drug in the range of about 30% to about 40% (weight/weight) based on the mass ratio of targeting agent, imaging agent, stabilizing agent or anticancer drug to the polymer conjugate. In some embodiments, including those of this paragraph, the total amount of targeting agent, imaging agent, stabilizing agent or anticancer drug present in the starting polymer conjugate and the total amount of targeting agent, imaging agent, stabilizing agent or anticancer drug present in the purified polymer conjugate can be approximately the same (such as, a total amount of targeting agent, imaging agent, stabilizing agent or anticancer drug in the range of about 20% to about 40%).

The total number of recurring units present in a polyanionic polymer conjugate described herein can vary. For example, the total number of recurring units of Formula (Ia) and (IIa) present in a poly(L-γ-glutamyl-glutamate)-anticancer drug conjugate described herein can vary over a broad range. In some embodiments, the total number of recurring units can be in the range of from about 40 to about 1,000. In some embodiments, the total number of recurring units can be in the range of from about 50 to about 500. In some embodiments, including those of this paragraph, the total number of recurring units present in the starting polymer conjugate and the total number of recurring units present in the purified polymer conjugate can be approximately the same (for example, the total number of recurring units in the range of from about 40 to about 1,000).

The targeting agent, imaging agent, stabilizing agent or anticancer drug may be conjugated to the polymer in many different ways. In some embodiments, the targeting agent, imaging agent, stabilizing agent or anticancer drug can be directly attached to the polymer through an oxygen, a sulfur, a nitrogen and/or carbon atom of the targeting agent, imaging agent, stabilizing agent or anticancer drug. In other embodiments, the targeting agent, imaging agent, stabilizing agent or anticancer drug can further include a linker group. A linker group is a group that attaches the targeting agent, imaging agent, stabilizing agent or anticancer drug to the polymer. For example, the targeting agent, imaging agent, stabilizing agent or anticancer drug can be attached to a recurring unit of Formula (Ia) via a linker group to form a recurring unit of Formula (IIa). The linker group may be relatively small. For instance, the linker group may include an amine, an amide, an ether, an ester, a hydroxyl group, a carbonyl group, or a thiol group. Alternatively, the linker group may be relatively large. For instance, the linker group may include an alkyl group, an alkoxy group, an aryl group, an aryl($C_{1-6}$alkyl) group, a heteroaryl group, or a heteroaryl ($C_{1-6}$alkyl) group. In one embodiment, the linker can be —NH(CH$_2$)$_{1-4}$—NH—. In some embodiments, the linker can be —(CH$_2$)$_{1-4}$-aryl-NH—. The linker group can be attached to the anticancer drug at any suitable position. For example, the linker group can be attached in place of a hydrogen at a carbon of the anticancer drug. The linker group can be added to the anticancer drug using methods known to those skilled in the art. In some embodiments, when the anticancer drug is paclitaxel, the paclitaxel can be conjugated via the oxygen atom attached to the C2'-carbon of the paclitaxel. In some embodiments, when the anticancer drug is paclitaxel, the paclitaxel can be conjugated via the oxygen atom attached to the C7-carbon of the paclitaxel.

A polyanionic polymer conjugate described herein (for example, poly(L-γ-glutamyl-glutamate) conjugate) can have various molecular weights. In some embodiments, a polyanionic polymer conjugate can have a weight average molecular weight in the range of about 10 kDa to about 150 kDa. In other embodiments, a polyanionic polymer conjugate can have a weight average molecular weight in the range of about 30 kDa to about 120 kDa. In still other embodiments, a polyanionic polymer conjugate can have a weight average molecular weight in the range of about 60 kDa to about 100 kDa. In yet still other embodiments, a polyanionic polymer conjugate can have a weight average molecular weight equal to or less than about 100 kDa. In some embodiments, a polyanionic polymer conjugate can have a weight average molecular weight equal to or greater than about 60 kDa. In some embodiments, including those of this paragraph, the weight average molecular weight of the starting polyanionic polymer conjugate and the weight average molecular weight of the purified polyanionic polymer conjugate can be approximately the same (for example, a weight average molecular weight in the range of about 70 kDa to about 85 kDa).

A polyanionic polymer conjugate described herein can have a narrow polydispersity index. For example, in some embodiments, the polydispersity index of a polymer conjugate (for example, poly(L-γ-glutamyl-glutamate)-anticancer drug conjugate) can be less than 2.0. In some embodiments, the polydispersity index of a polymer conjugate can be less than 1.7. In other embodiments, the polydispersity index of a polymer conjugate can be in the range of about 1.2 to about 2.0. In some embodiments, including those of this paragraph, the polydispersity index of the starting polymer conjugate and the polydispersity index of the purified polymer conjugate can be approximately the same (such as a polydispersity index in the range of about 1.2 to about 2.0).

Polyanionic polymers described herein can be obtained commercially or prepared using methods known to those skilled in the art. For example, poly(asparate) and poly (glutamate) can be obtained commercially. PGGA and PGAA can be prepared using method described in U.S. Publication No 2007/0128118, which hereby is incorporated by reference for the limited purpose of preparing PGGA, PGGA, and copolymers that include recurring units of Formula (A) and recurring units of Formula (B).

EXAMPLES

Example 1

According to a Phase I clinical trial, the endotoxin content should be controlled at the level less than 0.23 EU/mg to reach the calculated maximum dose administration (1500 mg per dose). The conventional approach of treating the PGGA-anticancer drug conjugate with activated carbon was not effective in reducing the amount of endotoxins. Conversion of water-soluble PGGA-PTX salt form (0.5 g) to water-insoluble PGGA-PTX acid form through acid precipitation followed by additional washing with ethanol/water, demonstrated that endotoxin levels were significantly reduced through this process (~83%).

Water-soluble PGGA-PTX salt form (30 g) was converted to PGGA-PTX acid form in an ethanol/HCl medium. The precipitate of PGGA-PTX acid form was washed twice by ethanol/water. After drying, the endotoxin level of the isolated PGGA-PTX acid form was analyzed and subjected to a full quality control (QC). The results showed that about 95% of the endotoxins were removed with no significant impact on the physiochemical properties of the isolated material.

The purified PGGA-PTX acid form was converted back to water-soluble PGGA-PTX salt form through basification by NaHCO$_3$ and purification with TFF. High quality water (MilliQ water) was utilized throughout the process. The endotoxin content of the processed water-soluble PGGA-PTX salt form was 0.12 EU/mg, which was well below the criterion (0.23 EU/mg). All physiochemical properties of the processed water-soluble PGGA-PTX salt form were comparable to those of the original material. Thus, the endotoxin level in the water-soluble PGGA-PTX salt form can be effectively reduced using this process.

Example 2

Conversion of PGGA-PTX Salt Form to Acid Form

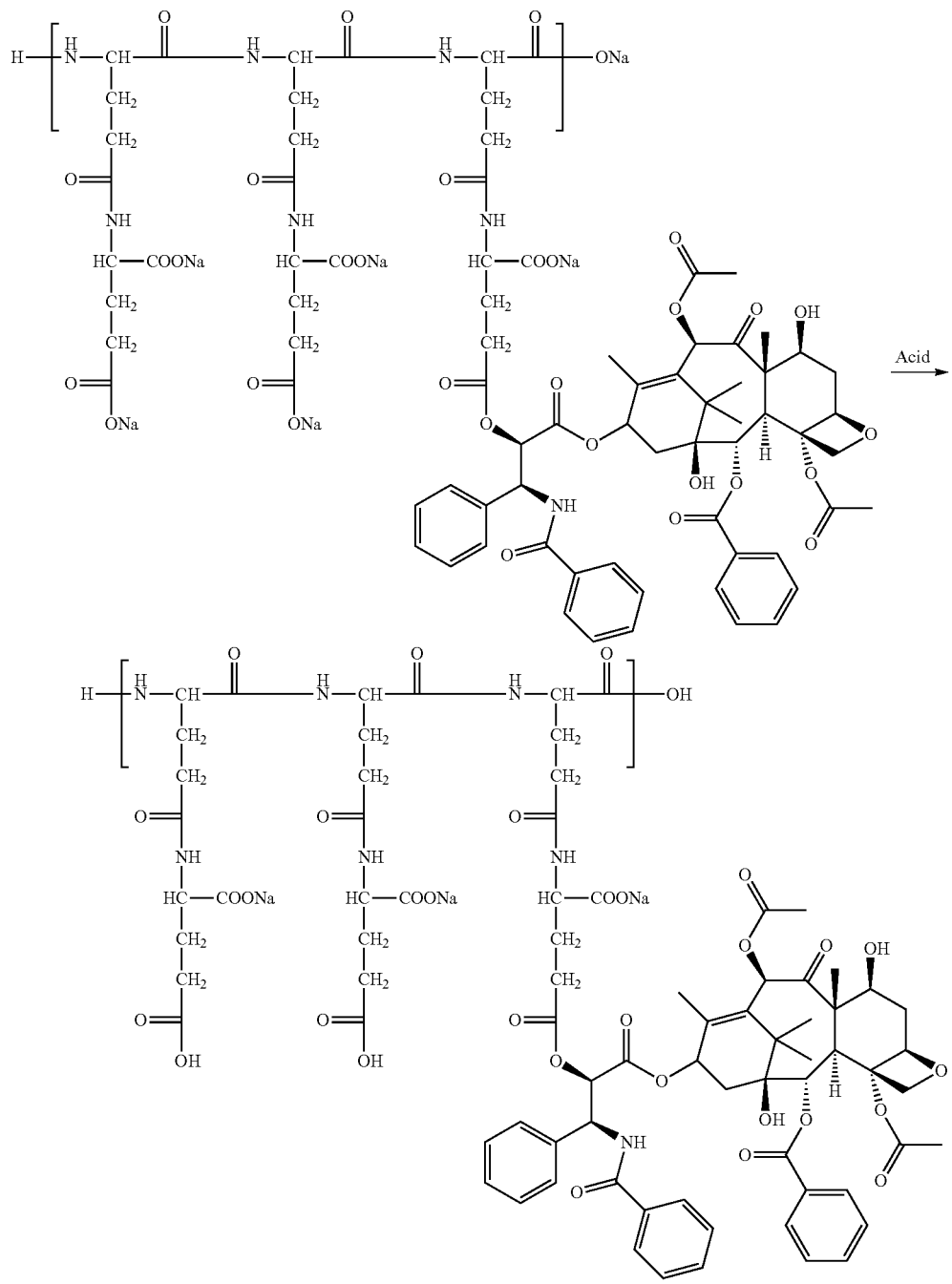

Ethanol (375 mL) was added to the PGGA-PTX solution, and the resulting solution was mixed. The solution was acidified with 1N HCl (78 mL) (prepared using MilliQ water) by vigorously stirring at 0-5° C. until the pH of the solution was approximately 2.5. The solution was stirred for 30 minutes, and the precipitate was isolated by centrifugation at 4° C. for 10 minutes at 6000 rpm. The sediment was PGGA-PTX salt form (30 g) was dissolved in MilliQ water (750 mL) to form a 40 mg/mL solution at room temperature. The mixture was stirred for about an hour until all solids were dissolved. The pH of the solution was measured as 7.41. The solution was filtered using a 0.2 μm membrane and then cooled to 0-5° C. using an ice bath.

resuspended in 1M HCl/ethanol (2:1) (1200 mL) and then agitated on a shaker for 10 minutes. The solid was isolated by centrifugation at 4° C. for 10 minutes at 6000 rpm. The isolated solid was resuspended a second time in 1M HCl/ethanol (2:1) (1200 mL) and then agitated on a shaker for 10 minutes. The solid was isolated by centrifugation at 4° C. for 10 minutes at 6000 rpm. The isolated solid was resuspended in MilliQ water and then agitated on a shaker for 10 minutes. The solid was isolated by centrifugation at 4° C. for 10 minutes at 6000 rpm. The isolated solid was lyophilized to a constant weight. PGGA-PTX acid form (26.7 g, 98.2%) was obtained. The dried PGGA-PTX acid form was submitted for a full quality control test and the endotoxin content was analyzed using an Endosafe® kit.

Example 3

Conversion of Acid Form of PGGA-PTX to Salt Form

Method A

PGGA-PTX acid form (10 g) was dissolved in 0.3 N NaHCO$_3$ solution (1000 mL) in a 6 L Erlenmeyer flask at 22° C. After the solid was dissolved, the resulting solution was stirred vigorously for 1 hour and the pH was recorded. The solution was diluted to 4 L using MilliQ water. The solution was purified using a 10 kDa mPES hollow fiber column on the MicroKros TFF system until the permeate conductivity was less than 0.05 mS/cm. The solution was then filtered with a 0.2 µM membrane filter. The endotoxin content was determined using GPC analysis. The solution was then frozen and lyophilized to a constant weight. The dried salt form was submitted for a full quality control test and endotoxin content analysis.

Method B

PGGA-PTX acid form (10 g) was dissolved in 0.3 N NaHCO$_3$ solution (1000 mL) in a 6 L Erlenmeyer flask at 22° C. A portion of the solution was extracted (50 mL) and allowed to stir for 6 hours at room temperature. The solution was transferred to dialysis tubing with 10 kDa MWCO. Dialysis was then performed 24 hrs using MilliQ water (for the first four hours of dialysis, MilliQ water was replaced every hour). The dialyzed solution was then filtered with a 0.2 µM membrane filter. The endotoxin content was determined using GPC analysis. The solution was then frozen and lyophilized to a constant weight. The dried salt form was submitted for a full quality control test and endotoxin content analysis.

Table 1 provides data on the starting and purified PGGA-PTX polymer conjugate. As shown in Table 1, the endotoxin level of the starting PGGA-anticancer drug conjugate in its salt form was 1.8 EU/mg. After conversion to its acid form, the endotoxin level was reduced to 0.11 EU/mg. After the acid form was converted back to the salt form, the endotoxin amount was determined to be 0.12 EU/mg. This data shows that the endotoxin amount was reduced by more than 16 fold. Table 1 also shows that physicochemical properties of PGGA-PTX suffered no negative effects, such as molecular weight, polydispersity index and drug loading.

TABLE 1

| Sample Type | Mw (kDa) | PDI | Drug Loading (GPC) | Endotoxin (EU/mg) |
| --- | --- | --- | --- | --- |
| PGGA-PTX salt form before purification | 79.9 | 1.645 | 36.7% | 1.8 |
| PGGA-PTX acid form | 79.8 | 1.621 | 37.1% | 0.11 |
| PGGA-PTX salt form after purification | 78.5 | 1.594 | 36.5% | 0.12 |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of purifying a polyanionic polymer conjugate comprising
   combining a starting polyanionic polymer conjugate with a first solvent system to form a solution;
   precipitating a portion of the starting polyanionic polymer conjugate by lowering the pH of the solution to be less than about 2.5; and
   washing the precipitated polyanionic polymer conjugate with a second solvent system,
   wherein the second solvent system comprises a water miscible organic solvent, to provide a purified polyanionic polymer conjugate,
   wherein the amount of endotoxin present in the purified polyanionic polymer conjugate is less than the amount of endotoxin present in the starting polyanionic polymer conjugate.

2. The method of claim 1, wherein the amount of endotoxin present in the purified polyanionic polymer conjugate is less than about 0.01 EU/mg.

3. The method of claim 1, wherein the amount of endotoxin is reduced in the range of about 100 fold to about 10 fold.

4. The method of claim 1, wherein the pH of the solution is lowered to be in the range of about 2.5 to about 1.5.

5. The method of claim 1, wherein the pH of the solution is lowered using one or more acids.

6. The method of claim 5, wherein the one or more acids is selected from the group consisting of hydrochloric acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phorsphoric acid, phosphorous acid and malonic acid.

7. The method of claim 1, wherein the first solvent system comprises one or more solvents.

8. The method of claim 7, wherein the first solvent system comprises water and/or at least one water miscible organic solvent.

9. The method of claim 8, wherein the water and the at least one water miscible organic solvent are added to the starting polyanionic polymer conjugate separately.

10. The method of claim 8, wherein the water miscible organic solvent is selected from the group consisting of acetaldehyde, acetone, acetonitrile, 1,2-butanediol, 1,3-butanediol, 1,4-butanediol, 2-butoxyethanol, dimethylformamide, dimethoxyethane, dimethyl sulfoxide, 1,4-dioxane, methanol, ethanol, ethylene glycol, furfuryl alcohol, glycerol, 1-propanol, isopropanol, 1,5-pentanediol, 1,3-propanediol, propylene glycol, tetrahydrofuran and triethylene glycol.

11. The method of claim 1, wherein the combining of the starting polyanionic polymer conjugate with the first solvent system is conducted at a temperature in the range of about 35° C. to about −5° C.

12. The method of claim 1, wherein the water miscible solvent is selected from the group consisting of acetaldehyde, acetone, acetonitrile, 1,2-butanediol, 1,3-butanediol, 1,4-butanediol, 2-butoxyethanol, dimethylformamide, dimethoxyethane, dimethyl sulfoxide, 1,4-dioxane, methanol, ethanol, ethylene glycol, furfuryl alcohol, glycerol, 1-propanol, isopropanol, 1,5-pentanediol, 1,3-propanediol, propylene glycol, tetrahydrofuran and triethylene glycol.

13. The method of claim 1, wherein the second solvent system further comprises one or more acids.

14. The method of claim 13, wherein the one or more acids is selected from the group consisting of hydrochloric acid, nitric acid, nitrous acid, sulfuric acid, sulfonic acid, acetic acid, formic acid, trichloroacetic acid, dichloroacetic acid, chloroacetic acid, glyoxylic acid, oxalic acid, glycolic acid, phorsphoric acid, phosphorous acid and malonic acid.

15. The method of claim 1, further comprising repeating the washing with the second solvent system one or more times.

16. The method of claim 15, wherein the precipitated polyanionic polymer conjugate is isolated between each washing.

17. The method of claim 1, further comprising repeating the washing with the second solvent system two or more times.

18. The method of claim 1, further comprising repeating the washing with the second solvent system that is repeated at least three times.

19. The method of claim 1, wherein the washing is performed by mixing the precipitated polyanionic polymer conjugate in the second solvent system.

20. The method of claim 1, further comprising repeating the washing with the second solvent system one or more times, wherein the second solvent system is the same for at least two of the washings.

21. The method of claim 1, further comprising repeating the washing with the second solvent system two or more times, wherein the second solvent system is different for at least two of the washings.

22. The method of claim 1, further comprising washing the precipitated polyanionic polymer conjugate with a third solvent system.

23. The method of claim 22, wherein the third solvent system comprises water and/or at least one water miscible organic solvent.

24. The method of claim 22, wherein the washing is performed by mixing the precipitated polyanionic polymer conjugate in the third solvent system.

25. The method of claim 1, further comprising drying the purified polyanionic polymer conjugate.

26. The method of claim 25, wherein the drying is performed by freeze drying.

27. The method of claim 1, further comprising isolating the precipitated polyanionic polymer conjugate before the washing.

28. The method of claim 27, wherein the isolating is performed by using one or more selected from membrane filter, molecular sieve, filter paper, chromatography, centrifugation.

29. The method of claim 1, further comprising filtering the solution before the lowering of the pH.

30. The method of claim 29, wherein the filtering is performed by using one or more selected from membrane filter, molecular sieve, filter paper, chromatography, centrifugation.

31. The method of claim 1, wherein the starting polyanionic-polymer conjugate is in its salt form.

32. The method of claim 1, wherein the precipitated portion of the starting polyanionic polymer conjugate is in its acid form.

33. The method of claim 1, further comprising forming an alkali metal salt of the precipitated polyanionic polymer conjugate after the washing.

34. The method of claim 1, wherein the starting polyanionic-polymer conjugate and the purified polyanionic polymer conjugate is a poly(L-γ-glutamyl-glutamate)-polymer conjugate, a poly(L-γ-glutamyl-aspartate)-polymer conjugate, a poly(aspartate)-polymer conjugate, or a poly(glutamate)-polymer conjugate.

35. The method of claim 34, wherein the starting polyanionic-polymer conjugate and the purified polyanionic polymer conjugate is a polyanionic anticancer drug conjugate.

36. The method of claim 34, wherein the poly(glutamate)-polymer conjugate comprises one or more recurring units of Formula (F1):

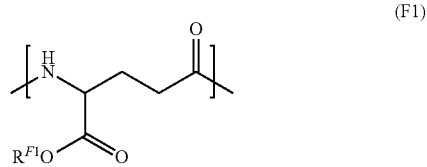

wherein $R^{F1}$ is a targeting agent, an imaging agent, a stabilizing agent or an anticancer drug.

37. The method of claim 36, wherein the poly(glutamate)-polymer conjugate is a copolymer conjugate that further comprises at least one recurring unit of Formula (F2):

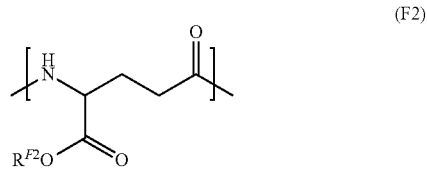

wherein $R^{F2}$ is hydrogen or an alkali metal.

38. The method of claim 37, wherein the anticancer drug is paclitaxel.

39. The method of claim 1, wherein the starting polyanionic-polymer conjugate and the purified polyanionic-polymer conjugate comprise one or more recurring units of Formula (Ia) and one or more recurring units of Formula (IIa):

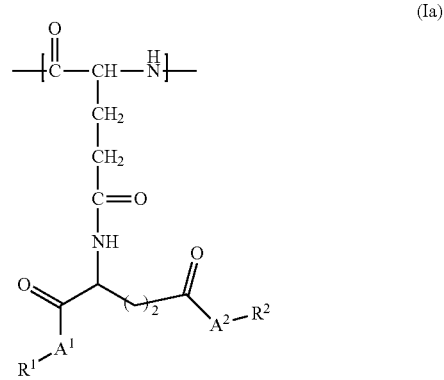

-continued

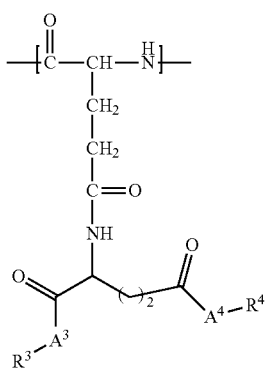

(IIa)

wherein:
  each $A^1$, each $A^2$, each $A^3$ and each $A^4$ are independently O or NH;
  each $R^1$ and each $R^2$ are independently hydrogen or an alkali metal; and
  each $R^3$ and each $R^4$ are independently hydrogen, an alkali metal, a targeting agent, an imaging agent, a stabilizing agent or an anticancer drug, provided that one of $R^3$ and $R^4$ is a targeting agent, an imaging agent, a stabilizing agent or an anticancer drug and the other of $R^3$ and $R^4$ is hydrogen or an alkali metal; or
  one or more recurring units of Formula (Ib) and one or more recurring units of Formula (IIb):

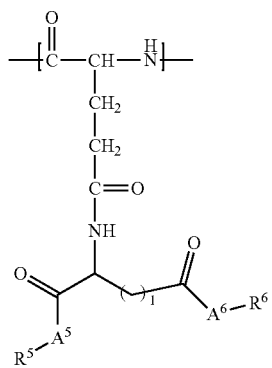

(Ib)

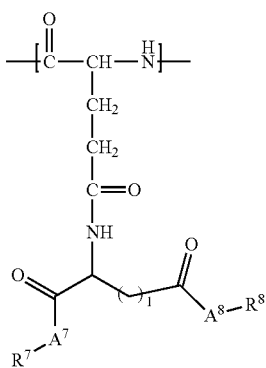

(IIb)

wherein:
  each $A^5$, each $A^6$, each $A^7$ and each $A^8$ are independently O or NH;
  each $R^5$ and each $R^6$ are independently hydrogen or an alkali metal; and
  each $R^7$ and each $R^8$ are independently hydrogen, an alkali metal, a targeting agent, an imaging agent, a stabilizing agent or an anticancer drug, provided that one of $R^7$ and $R^8$ is a targeting agent, an imaging agent, a stabilizing agent or an anticancer drug and the other of $R^7$ and $R^8$ is hydrogen or an alkali metal; or
  one or more recurring units of Formula (Ic) and one or more recurring units of (IIc):

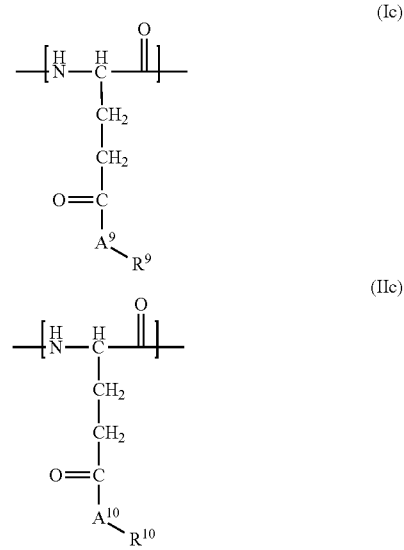

(Ic)

(IIc)

wherein:
  each $A^9$ and each $A^{10}$ are independently O or NH;
  each $R^9$ is hydrogen or an alkali metal; and
  each $R^{10}$ is a targeting agent, an imaging agent, a stabilizing agent or an anticancer drug; or
  one or more recurring units of Formula (Id) and one or more recurring units of (IId):

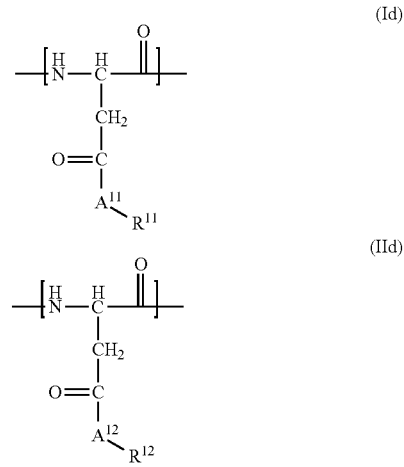

(Id)

(IId)

wherein:
  each $A^{11}$ and each $A^{12}$ are independently O or NH;
  each $R^{11}$ is independently hydrogen or an alkali metal; and each $R^{12}$ is a targeting agent, an imaging agent, a stabilizing agent or an anticancer drug; or one or more recurring units of Formula (Ie) and one or more recurring units of (IIe):

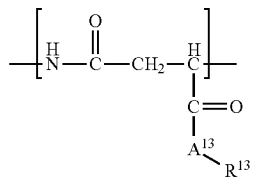
(Ie)

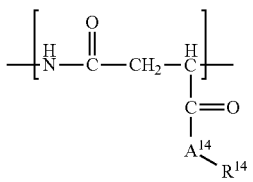
(IIe)

wherein:
each $A^{13}$ and each $A^{14}$ are independently O or NH;
each $R^{13}$ is independently hydrogen or an alkali metal; and
each $R^{14}$ is a targeting agent, an imaging agent, a stabilizing agent or an anticancer drug.

40. The method of claim 39, wherein the starting polyanionic-polymer conjugate and the purified polyanionic-polymer conjugate are a copolymer conjugate comprising one or more recurring units selected from Formulae (Ia), (Ib), (Ic), (Id), and (Ie), and one or more recurring units selected from Formulae (IIa), (IIb), (IIc), (IId), and (IIe), provided that the copolymer does not consist only of recurring units of (Ia) and (IIa), (Ib) and (IIb), (Ic) and (IIc), (Id) and (IId), (Ie) and (IIe), or (Id), (IId), (Ie) and (IIe).

41. The method of claim 39, wherein the alkali metal is sodium.

42. The method of claim 39, wherein the starting polyanionic-polymer conjugate and the purified polyanionic-polymer conjugate is polyanionic-anticancer drug conjugate; and the anticancer drug is paclitaxel.

* * * * *